US009161684B2

(12) United States Patent
Seibel et al.

(10) Patent No.: US 9,161,684 B2
(45) Date of Patent: Oct. 20, 2015

(54) MONITORING DISPOSITION OF TETHERED CAPSULE ENDOSCOPE IN ESOPHAGUS

(75) Inventors: Eric J. Seibel, Seattle, WA (US); Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 1427 days.

(21) Appl. No.: 11/852,227

(22) Filed: Sep. 7, 2007

(65) Prior Publication Data

US 2007/0299309 A1 Dec. 27, 2007

Related U.S. Application Data

(63) Continuation-in-part of application No. 11/069,826, filed on Feb. 28, 2005, now Pat. No. 7,530,948.

(51) Int. Cl.
*A61B 1/273* (2006.01)
*A61B 1/00* (2006.01)
(Continued)

(52) U.S. Cl.
CPC ............. *A61B 1/2733* (2013.01); *A61B 1/0008* (2013.01); *A61B 1/00172* (2013.01); *A61B 1/0638* (2013.01); *A61B 1/07* (2013.01); *A61B 5/0084* (2013.01); *A61B 5/1455* (2013.01);
(Continued)

(58) Field of Classification Search
CPC ............... A61B 1/2733; A61B 1/0008; A61B 1/00172; A61B 1/07; A61B 1/0638; A61B 1/043; A61B 1/041; A61B 5/0084; A61B 5/1455; A61B 5/4233; A61B 5/0068; A61B 5/0071; A61B 5/0075; A61B 5/14556

USPC .................. 600/104, 114, 120, 117, 424, 129
See application file for complete search history.

(56) References Cited

U.S. PATENT DOCUMENTS 4,085,742 A * 4/1978 Okada ........................... 600/112
4,118,270 A 10/1978 Pan et al. ....................... 156/659
(Continued)

FOREIGN PATENT DOCUMENTS

DE 4428967 12/1995 ............. A61B 17/36
EP 0 713 672 5/1996 ............... A61B 1/00
(Continued)

OTHER PUBLICATIONS

Translation of JP 20030088499, Mar. 2003.*
(Continued)

*Primary Examiner* — John P Leubecker
(74) *Attorney, Agent, or Firm* — Wilson Sonsini Goodrich & Rosati

(57) ABSTRACT

A scanning flexible endoscope includes a tether attached to a capsule. The tether controls a disposition of the capsule within a body lumen such as the esophagus. A scanning device in the capsule optically scans the adjacent tissue on the inside surface of the body lumen as the capsule is moved axially through the body lumen. A non-contact sensor responds to indicia on the tether to measure a relative position of the tether and the capsule in the body lumen. The indicia can be analog or digital in form and the sensor can be either magnetic, or optical. A wiper is optionally provided to remove bodily fluids from the tether when pulled from the body lumen past the sensor. A pulse of fluid can be delivered to the distal end of the tether to cause the body lumen to distend, facilitating free movement of the capsule in the lumen.

28 Claims, 19 Drawing Sheets

(51) Int. Cl.
*A61B 1/07* (2006.01)
*A61B 5/1455* (2006.01)
*A61B 1/06* (2006.01)
*A61B 1/04* (2006.01)
*A61B 5/00* (2006.01)

(52) U.S. Cl.
CPC .............. *A61B 5/4233* (2013.01); *A61B 1/041* (2013.01); *A61B 1/043* (2013.01); *A61B 5/0068* (2013.01); *A61B 5/0071* (2013.01); *A61B 5/0075* (2013.01); *A61B 5/14556* (2013.01)

(56) References Cited

U.S. PATENT DOCUMENTS

| | | | |
|---|---|---|---|
| 4,234,788 A | 11/1980 | Palmer et al. | 250/227 |
| 4,265,699 A | 5/1981 | Ladany | 156/657 |
| 4,410,235 A | 10/1983 | Klement et al. | 350/96.18 |
| 4,454,547 A | 6/1984 | Yip et al. | 358/293 |
| 4,681,093 A * | 7/1987 | Ono et al. | 600/116 |
| 4,686,963 A | 8/1987 | Cohen et al. | 128/4 |
| 4,688,555 A | 8/1987 | Wardle | 128/4 |
| 4,695,163 A | 9/1987 | Schachar | 356/369 |
| 4,710,619 A | 12/1987 | Haberl | 250/203 |
| 4,743,283 A | 5/1988 | Borsuk | 65/2 |
| 4,758,222 A | 7/1988 | McCoy | 604/95 |
| 4,762,118 A | 8/1988 | Lia et al. | 128/4 |
| 4,768,513 A | 9/1988 | Suzuki | 128/634 |
| 4,782,228 A | 11/1988 | Westell | 250/236 |
| 4,804,395 A | 2/1989 | Clark et al. | 65/2 |
| 4,824,195 A | 4/1989 | Khoe | 350/96.18 |
| 4,850,364 A | 7/1989 | Leavitt | 128/661.09 |
| 4,928,316 A | 5/1990 | Heritage et al. | 455/600 |
| 4,951,048 A * | 8/1990 | Ichikawa et al. | 341/15 |
| 4,971,035 A * | 11/1990 | Ito | 600/129 |
| 4,979,496 A | 12/1990 | Komi | 128/4 |
| 4,983,165 A | 1/1991 | Loiterman | 604/94 |
| 5,037,174 A | 8/1991 | Thompson | 385/33 |
| 5,074,642 A | 12/1991 | Hicks | 385/116 |
| 5,103,497 A | 4/1992 | Hicks | 385/117 |
| 5,172,685 A | 12/1992 | Nudelman | 128/6 |
| 5,209,117 A | 5/1993 | Bennett | 73/517 |
| 5,231,286 A | 7/1993 | Kajimura et al. | 250/234 |
| 5,247,174 A | 9/1993 | Berman | 250/235 |
| 5,272,330 A | 12/1993 | Betzig et al. | 250/216 |
| 5,286,970 A | 2/1994 | Betzig et al. | 250/227.26 |
| 5,305,759 A | 4/1994 | Kaneko et al. | 600/476 |
| 5,321,501 A | 6/1994 | Swanson et al. | 356/345 |
| 5,360,968 A | 11/1994 | Scott | 235/454 |
| 5,363,135 A * | 11/1994 | Inglese | 348/70 |
| 5,381,782 A | 1/1995 | DeLaRama et al. | 128/4 |
| 5,394,500 A | 2/1995 | Marchman | 385/123 |
| 5,405,337 A | 4/1995 | Maynard | 604/281 |
| 5,425,123 A | 6/1995 | Hicks | 385/117 |
| 5,459,803 A | 10/1995 | Yamane et al. | 385/33 |
| 5,480,046 A | 1/1996 | Filas et al. | 216/7 |
| 5,507,725 A | 4/1996 | Savage et al. | 604/95 |
| 5,512,035 A | 4/1996 | Konstorum et al. | 600/146 |
| 5,535,759 A | 7/1996 | Wilk | 128/898 |
| 5,549,542 A | 8/1996 | Kovalcheck | 600/146 |
| 5,563,969 A | 10/1996 | Honmou | 385/35 |
| 5,570,441 A | 10/1996 | Filas et al. | 385/43 |
| 5,575,754 A * | 11/1996 | Konomura | 600/117 |
| 5,627,922 A | 5/1997 | Kopelman et al. | 385/12 |
| 5,643,175 A * | 7/1997 | Adair | 600/133 |
| 5,649,897 A | 7/1997 | Nakamura | 600/111 |
| 5,668,644 A | 9/1997 | Kuroiwa et al. | 358/480 |
| 5,703,979 A | 12/1997 | Filas et al. | 385/43 |
| 5,715,337 A | 2/1998 | Spitzer et al. | 385/4 |
| 5,724,169 A | 3/1998 | LaGasse | 359/173 |
| 5,727,098 A | 3/1998 | Jacobson | 385/31 |
| 5,765,561 A | 6/1998 | Chen et al. | 128/653.1 |
| 5,894,122 A | 4/1999 | Tomita | 250/234 |
| 5,906,620 A | 5/1999 | Nakao et al. | 606/113 |
| 5,919,200 A | 7/1999 | Stambaugh et al. | 606/159 |
| 5,939,709 A | 8/1999 | Ghislain et al. | 250/216 |
| 5,947,905 A | 9/1999 | Hadjicostis et al. | 600/463 |
| 5,957,833 A * | 9/1999 | Shan | 600/117 |
| 5,984,860 A | 11/1999 | Shan | 600/116 |
| 5,991,697 A | 11/1999 | Nelson et al. | 702/49 |
| 6,035,229 A | 3/2000 | Silverstein et al. | 600/473 |
| 6,046,720 A | 4/2000 | Melville et al. | 345/108 |
| 6,069,698 A | 5/2000 | Ozawa et al. | 356/345 |
| 6,081,605 A | 6/2000 | Roth et al. | 382/103 |
| 6,091,067 A | 7/2000 | Drobot et al. | 250/234 |
| 6,096,054 A | 8/2000 | Wyzgala et al. | 606/170 |
| 6,097,528 A | 8/2000 | Lebby et al. | 359/251 |
| 6,134,003 A | 10/2000 | Tearney et al. | 356/479 |
| 6,142,957 A | 11/2000 | Diamond et al. | 600/567 |
| 6,148,095 A | 11/2000 | Prause et al. | 382/131 |
| 6,161,035 A | 12/2000 | Furusawa | 600/476 |
| 6,169,281 B1 | 1/2001 | Chen et al. | 250/234 |
| 6,185,443 B1 | 2/2001 | Crowley | 600/407 |
| 6,191,862 B1 | 2/2001 | Swanson et al. | 356/450 |
| 6,211,904 B1 | 4/2001 | Adair et al. | 348/76 |
| 6,215,437 B1 | 4/2001 | Schurmann et al. | 342/42 |
| 6,240,312 B1 | 5/2001 | Alfano et al. | 600/476 |
| 6,241,657 B1 | 6/2001 | Chen et al. | 600/117 |
| 6,246,914 B1 | 6/2001 | de la Rama et al. | 607/122 |
| 6,289,144 B1 | 9/2001 | Neuschafer et al. | 385/12 |
| 6,294,775 B1 | 9/2001 | Seibel et al. | 250/208.1 |
| 6,327,493 B1 | 12/2001 | Ozawa et al. | 600/476 |
| 6,370,422 B1 | 4/2002 | Richards-Kortum et al. | 600/478 |
| 6,387,119 B2 | 5/2002 | Wolf et al. | 623/1.11 |
| 6,441,359 B1 | 8/2002 | Cozier et al. | 250/216 |
| 6,443,894 B1 | 9/2002 | Sumanaweera et al. | 600/443 |
| 6,461,337 B1 | 10/2002 | Minotti et al. | 604/264 |
| 6,466,687 B1 | 10/2002 | Uppaluri et al. | 382/128 |
| 6,485,413 B1 | 11/2002 | Boppart et al. | 600/160 |
| 6,515,274 B1 | 2/2003 | Moskovits et al. | 250/216 |
| 6,515,781 B2 | 2/2003 | Lewis et al. | 359/204 |
| 6,525,310 B2 | 2/2003 | Dunfield | 250/235 |
| 6,545,260 B1 | 4/2003 | Katashiro | 250/227.26 |
| 6,546,271 B1 | 4/2003 | Reisfeld | 600/407 |
| 6,549,801 B1 | 4/2003 | Chen et al. | 600/425 |
| 6,550,918 B1 | 4/2003 | Agostinelli et al. | 353/7 |
| 6,563,105 B2 | 5/2003 | Seibel et al. | 250/208.1 |
| 6,563,998 B1 | 5/2003 | Farah et al. | 385/131 |
| 6,564,087 B1 | 5/2003 | Pitris et al. | 600/478 |
| 6,564,089 B2 | 5/2003 | Izatt et al. | 600/478 |
| 6,612,980 B2 | 9/2003 | Chen et al. | 600/117 |
| 6,615,072 B1 | 9/2003 | Izatt et al. | 600/478 |
| 6,678,541 B1 | 1/2004 | Durkin et al. | 600/310 |
| 6,685,718 B1 | 2/2004 | Wyzgala et al. | 606/170 |
| 6,687,010 B1 | 2/2004 | Horii et al. | 356/479 |
| 6,689,064 B2 | 2/2004 | Hager et al. | 600/454 |
| 6,690,963 B2 | 2/2004 | Ben-Haim et al. | 600/424 |
| 6,694,983 B2 | 2/2004 | Wolf et al. | 128/898 |
| 6,726,675 B1 * | 4/2004 | Beyar | 604/510 |
| 6,735,463 B2 | 5/2004 | Izatt et al. | 600/476 |
| 6,755,532 B1 | 6/2004 | Cobb | 353/7 |
| 6,773,394 B2 | 8/2004 | Taniguchi et al. | 600/117 |
| 6,779,892 B2 | 8/2004 | Agostinelli et al. | 353/7 |
| 6,785,571 B2 | 8/2004 | Glossop | 600/424 |
| 6,788,967 B2 | 9/2004 | Ben-Haim et al. | 600/424 |
| 6,818,001 B2 | 11/2004 | Wulfman et al. | 606/159 |
| 6,826,342 B1 | 11/2004 | Bise et al. | 385/125 |
| 6,832,984 B2 | 12/2004 | Stelzer et al. | 604/93.01 |
| 6,836,560 B2 | 12/2004 | Emery | 382/145 |
| 6,839,586 B2 | 1/2005 | Webb | 600/478 |
| 6,845,190 B1 | 1/2005 | Smithwick et al. | 385/25 |
| 6,856,712 B2 | 2/2005 | Fauver et al. | 385/12 |
| 6,858,005 B2 | 2/2005 | Ohline et al. | 600/141 |
| 6,866,626 B2 * | 3/2005 | Long et al. | 600/114 |
| 6,872,433 B2 | 3/2005 | Seward et al. | 428/36.9 |
| 6,882,429 B1 | 4/2005 | Weitekamp et al. | 356/482 |
| 6,889,175 B2 | 5/2005 | Green | 702/190 |
| 6,892,090 B2 | 5/2005 | Verard et al. | 600/424 |
| 6,902,528 B1 | 6/2005 | Garibaldi et al. | 600/118 |
| 6,932,829 B2 | 8/2005 | Majercak | 606/198 |
| 6,975,898 B2 | 12/2005 | Seibel et al. | 600/473 |
| 7,004,173 B2 | 2/2006 | Sparks et al. | 128/898 |
| 7,023,558 B2 | 4/2006 | Fee et al. | 356/489 |
| 7,038,191 B2 | 5/2006 | Kare et al. | 250/227.11 |

(56) References Cited

U.S. PATENT DOCUMENTS

| | | | |
|---|---|---|---|
| 7,072,046 B2 | 7/2006 | Xie et al. | 356/479 |
| 7,158,234 B2 | 1/2007 | Uchiyama et al. | 356/479 |
| 7,170,610 B2 | 1/2007 | Knuttel | 356/456 |
| 7,179,220 B2 | 2/2007 | Kukuk | 600/118 |
| 7,189,961 B2 | 3/2007 | Johnston et al. | 250/234 |
| 7,252,674 B2 | 8/2007 | Wyzgala et al. | 606/170 |
| 7,261,687 B2 | 8/2007 | Yang | 600/173 |
| 7,324,211 B2 | 1/2008 | Tsujita | 356/497 |
| 7,349,098 B2 | 3/2008 | Li et al. | 356/479 |
| 7,366,376 B2 | 4/2008 | Shishkov et al. | 385/35 |
| 7,404,929 B2 | 7/2008 | Fulghum, Jr. | 422/82.05 |
| 7,447,408 B2 | 11/2008 | Bouma et al. | 385/123 |
| 7,515,274 B2 | 4/2009 | Gelikonov et al. | 356/479 |
| 7,530,948 B2 | 5/2009 | Seibel et al. | 600/102 |
| 7,615,005 B2 | 11/2009 | Stefanchik et al. | 600/106 |
| 7,616,986 B2 | 11/2009 | Seibel et al. | 600/476 |
| 7,747,312 B2 | 6/2010 | Barrick et al. | 600/426 |
| 7,783,337 B2 | 8/2010 | Feldman et al. | 600/160 |
| 2001/0030744 A1 | 10/2001 | Chang et al. | 356/73 |
| 2001/0055462 A1 | 12/2001 | Seibel | |
| 2002/0013512 A1* | 1/2002 | Sendai et al. | 600/160 |
| 2002/0071625 A1 | 6/2002 | Bartholomew et al. | 385/12 |
| 2002/0091325 A1 | 7/2002 | Ostrovsky | 600/478 |
| 2002/0183592 A1* | 12/2002 | Suzuki et al. | 600/145 |
| 2003/0009189 A1 | 1/2003 | Gilson et al. | 606/200 |
| 2003/0032878 A1 | 2/2003 | Shahidi | 600/429 |
| 2003/0045778 A1 | 3/2003 | Ohline et al. | 600/117 |
| 2003/0055317 A1 | 3/2003 | Taniguchi et al. | 600/117 |
| 2003/0060734 A1 | 3/2003 | Yokoi et al. | |
| 2003/0103199 A1 | 6/2003 | Jung et al. | 356/73 |
| 2003/0103665 A1 | 6/2003 | Uppaluri et al. | 382/131 |
| 2003/0142934 A1 | 7/2003 | Pan et al. | 385/116 |
| 2003/0160721 A1 | 8/2003 | Gilboa et al. | 342/450 |
| 2003/0179428 A1 | 9/2003 | Suzuki et al. | 359/204 |
| 2003/0181788 A1 | 9/2003 | Yokoi et al. | |
| 2003/0208103 A1* | 11/2003 | Sonnenschein et al. | 600/117 |
| 2003/0208107 A1 | 11/2003 | Refael | 600/300 |
| 2003/0208134 A1 | 11/2003 | Secrest et al. | 600/562 |
| 2003/0216639 A1 | 11/2003 | Gilboa et al. | 600/424 |
| 2003/0220749 A1 | 11/2003 | Chen et al. | 702/31 |
| 2003/0236564 A1 | 12/2003 | Majercak | 623/1.11 |
| 2004/0015049 A1 | 1/2004 | Zarr | 600/101 |
| 2004/0015053 A1 | 1/2004 | Bieger et al. | 600/117 |
| 2004/0019254 A1* | 1/2004 | Belson et al. | 600/146 |
| 2004/0033006 A1 | 2/2004 | Farah | 385/14 |
| 2004/0061072 A1 | 4/2004 | Gu et al. | 250/458.1 |
| 2004/0118415 A1 | 6/2004 | Hall et al. | 128/898 |
| 2004/0147827 A1 | 7/2004 | Bowe | 600/374 |
| 2004/0176683 A1* | 9/2004 | Whitin et al. | 600/424 |
| 2004/0181148 A1 | 9/2004 | Uchiyama et al. | 600/425 |
| 2004/0199052 A1 | 10/2004 | Banik et al. | 600/142 |
| 2004/0243227 A1 | 12/2004 | Starksen et al. | 623/2.11 |
| 2004/0249267 A1 | 12/2004 | Gilboa | 600/204 |
| 2004/0260199 A1 | 12/2004 | Hardia et al. | 600/566 |
| 2005/0020878 A1 | 1/2005 | Ohnishi et al. | 600/117 |
| 2005/0020926 A1 | 1/2005 | Wiklof et al. | 600/476 |
| 2005/0036150 A1 | 2/2005 | Izatt et al. | 356/479 |
| 2005/0054931 A1 | 3/2005 | Clark | 600/453 |
| 2005/0065433 A1 | 3/2005 | Anderson | 600/424 |
| 2005/0085693 A1 | 4/2005 | Belson et al. | 600/146 |
| 2005/0111009 A1 | 5/2005 | Keightley et al. | 356/602 |
| 2005/0168751 A1 | 8/2005 | Horii et al. | 356/479 |
| 2005/0171438 A1 | 8/2005 | Chen et al. | 600/476 |
| 2005/0171592 A1 | 8/2005 | Majercak | 623/1.11 |
| 2005/0183733 A1 | 8/2005 | Kawano et al. | 128/899 |
| 2005/0206774 A1 | 9/2005 | Tsujimoto | 348/345 |
| 2005/0215854 A1 | 9/2005 | Ozaki et al. | 600/109 |
| 2005/0215911 A1 | 9/2005 | Alfano et al. | 600/476 |
| 2005/0228290 A1 | 10/2005 | Borovsky et al. | 600/466 |
| 2005/0250983 A1 | 11/2005 | Tremaglio et al. | 600/101 |
| 2005/0272975 A1 | 12/2005 | McWeeney et al. | 600/113 |
| 2006/0009679 A1* | 1/2006 | Ito et al. | 600/117 |
| 2006/0015126 A1 | 1/2006 | Sher | 606/159 |
| 2006/0030753 A1 | 2/2006 | Boutillette et al. | 600/146 |
| 2006/0052662 A1 | 3/2006 | Kress | 600/123 |
| 2006/0100480 A1 | 5/2006 | Ewers et al. | 600/114 |
| 2006/0126064 A1 | 6/2006 | Bambot et al. | 356/337 |
| 2006/0149134 A1 | 7/2006 | Soper et al. | 600/182 |
| 2006/0149163 A1 | 7/2006 | Hibner et al. | 600/566 |
| 2006/0161043 A1* | 7/2006 | Neumann et al. | 600/114 |
| 2006/0187462 A1 | 8/2006 | Srinivasan et al. | 356/479 |
| 2006/0202015 A1 | 9/2006 | Lizotte et al. | 250/234 |
| 2006/0252993 A1 | 11/2006 | Freed et al. | 600/146 |
| 2007/0038119 A1 | 2/2007 | Chen et al. | 600/476 |
| 2007/0066983 A1 | 3/2007 | Maschke | 606/159 |
| 2007/0088219 A1 | 4/2007 | Xie et al. | 600/473 |
| 2007/0093703 A1 | 4/2007 | Sievert et al. | 600/343 |
| 2007/0106114 A1* | 5/2007 | Sugimoto et al. | 600/117 |
| 2007/0129601 A1 | 6/2007 | Johnston et al. | 600/109 |
| 2007/0213618 A1 | 9/2007 | Li et al. | 600/476 |
| 2007/0270650 A1 | 11/2007 | Eno et al. | 600/145 |
| 2007/0276184 A1* | 11/2007 | Okawa | 600/117 |
| 2008/0004491 A1 | 1/2008 | Karasawa | 600/101 |
| 2008/0039685 A1* | 2/2008 | Komiya et al. | 600/106 |
| 2008/0161748 A1 | 7/2008 | Tolkoff et al. | |
| 2008/0221388 A1 | 9/2008 | Seibel et al. | 600/109 |

FOREIGN PATENT DOCUMENTS

| | | | |
|---|---|---|---|
| EP | 0 520 388 | 9/1996 | B41J 2/455 |
| EP | 1 077 360 | 2/2001 | G01B 9/02 |
| EP | 1 088 515 | 4/2001 | A61B 5/06 |
| EP | 1 142 529 | 10/2001 | A61B 1/00 |
| EP | 0 712 032 | 12/2001 | G03B 35/08 |
| EP | 1 310 206 | 5/2003 | A61B 1/015 |
| EP | 1 421 913 | 5/2004 | A61B 19/00 |
| EP | 0 910 284 | 1/2007 | A61B 10/00 |
| EP | 1 063 921 | 2/2007 | A61B 10/00 |
| JP | S 59-7919 A | 1/1984 | |
| JP | H 03-162818 A | 7/1991 | |
| JP | 05-154154 | 6/1993 | A61B 10/00 |
| JP | H 06-114036 A | 4/1994 | |
| JP | H 06-114037 A | 4/1994 | |
| JP | 06-511312 | 12/1994 | G01B 9/02 |
| JP | H 11-72431 A | 3/1999 | |
| JP | 2001-137182 A | 5/2001 | |
| JP | 2001174744 | 6/2001 | G02B 23/24 |
| JP | 2002-153419 A | 5/2002 | |
| JP | 2002-360508 A | 12/2002 | |
| JP | 2003-088499 A | 3/2003 | |
| JP | 2003-135387 A | 5/2003 | |
| JP | 2003-195186 A | 7/2003 | |
| JP | 2003-210395 A | 7/2003 | |
| JP | 2003-299613 A | 10/2003 | |
| JP | 2003-535622 A | 12/2003 | |
| JP | 2004-298560 A | 10/2004 | |
| JP | 2004-357870 A | 12/2004 | |
| JP | 2006-280857 A | 10/2006 | |
| JP | 2006-280858 A | 10/2006 | |
| JP | 2006-280859 A | 10/2006 | |
| WO | WO 93/20742 | 10/1993 | A61B 1/06 |
| WO | WO 96/02184 | 2/1996 | A61B 5/00 |
| WO | WO 98/38907 | 9/1998 | A61B 5/00 |
| WO | WO 98/43530 | 10/1998 | A61B 1/00 |
| WO | WO 99/04301 | 1/1999 | G02B 21/00 |
| WO | WO 01/97902 | 12/2001 | |
| WO | WO 03/041561 A2 | 5/2003 | |
| WO | WO 2004/010858 A2 | 2/2004 | |
| WO | WO 2005/024496 | 3/2005 | |
| WO | WO 2007/007724 A1 | 1/2007 | |

OTHER PUBLICATIONS

"Given® Diagnostic System." The Platform for PillCam™ Endoscopy 4pp. <http:www.givenimaging.com> Copyright © 2001-2004 Given Imaging Ltd. All Rights Reserved.

Martinez, O.E., "3000 Times Grating Compressor with Positive Group-Velocity Dispersion—Application to Fiber Compensation in 1.3-1.6 μm Region." *IEEE Journal of Quantum Electronics* vol. 23: 59-64, 1987.

Mori et al., "A Method for Tracking camera motion of real endoscope by using virtual endoscopy system." *Proceedings of SPIE*: 1-12, 2000. <www.http://www.toriwaki.nuie.nagoya-u.ac.jp> 12pp. 1-12.

(56) References Cited

OTHER PUBLICATIONS

Morofke et al., "Wide dynamic range detection of bidirectional flow in Doppler optical coherence tomography using a two-dimensional Kasai estimator." *Optics Letters*, vol. 32, No. 3: 253-255, Feb. 1, 2007.

Murakami et al., "A Miniature Confocal Optical Microscope With Mems Gimbal Scanner." *The 12th International Conference on Solid State Sensors, Actuators and Microsystems* Boston: 587-590, Jun. 8-12, 2003.

Myaing et al., "Enhanced two-photon biosensing with double-clad photonic crystal fibers," *Optics Letters*, vol. 28, No. 14: 1224-1226, 2003.

Ohmi et al., "Quasi In-Focus Optical Coherence Tomography." *Japanese Journal of Applied Physics* vol. 43, No. 2: 845-849, 2004.

Oikawa et al., "Intra-operative Guidance with Real-time Information of Open MRI and Manipulators Using Coordinate-Integration Module." *Proceedings of SPIE*, vol. 5029: 653-660, 2003.

Pagoulatos et al., "Image-based Registration of Ultrasound and Magnetic Resonance Images: A Preliminary Study." *Proceedings of SPIE*, vol. 3976: 156-164, 2000.

Patterson et al., "Applications of time-resolved light scattering measurements to photodynamic therapy dosimetry." *SPIE* vol. 1203, Photodynamic Therapy: Mechanism II: 62-75, 1990.

Pyhtila et al., "Determining nuclear morphology using an improved angle-resolved low coherence interferometry system." *Optics Express*, vol. 11, No. 25: 3473-3484, Dec. 15, 2003.

Pyhtila et al., "Fourier-domain angle-resolved low coherence interferometry through an endoscopic fiber bundle for light-scattering spectroscopy." *Optics Letters*, vol. 31, No. 6: 772-774, Dec. 1, 2005.

Pyhtila et al., "Rapid, depth-resolved light scattering measurements using Fourier domain, angle-resolved low coherence interferometry." *Optical Society of America*: 6pp, 2004.

Podoleanu et al., "Three dimensional OCT images from retina and skin." *Optics Express* vol. 7, No. 9: 292-298, 2000.

Qi et al., "Dynamic focus control in high-speed optical coherence tomography based on a microelectromechanical mirror." *Optics Communications* vol. 232: 123-128, 2004.

Russo et al., "Lens-ended Fibers for Medical Applications: A New Fabrication Technique." *Appl. Opt.* vol. 23, No. 19: 3277-3283, Oct. 1, 1984.

Sasaki et al., "Scanning Near-Field Optical Microscope using Cantilever Integrated with Light Emitting Diode, Waveguide, Aperture, and Photodiode." Optical MEMS 2000 Invited Speakers: Advance Program, Sponsored by IEEE Lasers and Electro-Optics Society: 16pp, 2000. Available at <http://www.ieee.org/organizations/society/leos/LEOSCONF/MEMS/omspeak.html.>.

Schmitt et al., "An optical coherence microscope with enhanced resolving power in thick tissue." *Optics Communications* 142: 203-207, 1997.

Schwartz et al., "Electromagnetic Navigation during Flexible Bronchoscopy." *Interventional Pulmonology: Respiration*, vol. 70: 516-522, 2003.

Seibel et al., "Unique Features of Optical Scanning, Single Fiber Endoscopy." *Lasers in Surgery and Medicine* vol. 30: 177-183, 2002.

Shahidi et al., "Implementation, Calibration and Accuracy Testing of an Image-Enhanced Endoscopy System." *IEEE Transactions on Medical Imaging*, vol. 21, No. 12: 1524-1535, 2002.

Shinagawa et al., "CT-Guided Transbronchial Biopsy Using an Ultrathin Bronchoscopic Navigation." *Chest*, vol. 125, No. 3: 1138-1143, 2003.

Shiraishi et al., "Spot Size Reducer for Standard Single-Mode Fibers Utilizing a Graded-Index Fiber Tip." *ECOC 97*: 50-53, Sep. 22-25, 1997.

Shoji et al., "Camera motion tracking of real endoscope by using virtual endoscopy system and texture information." *Proceedings of SPIE*, vol. 4321: 122-133, 2001.

Skala et al., "Multiphoton Microscopy of Endogenous Fluorescence Differentiates Normal, Precancerous, and Cancerous Squamous Epithelial Tissues." *Cancer Research* vol. 65, No. 4: 1180-1186, Feb. 15, 2005. Available at <www.aacrjournals.org>.

Smithwick et al., "Modeling and Control of the Resonant Fiber Scanner for Laser Scanning Display or Acquisition." *SID 03 DIGEST*: 1455-1457, 2003.

Solomon et al., "Three-dimensional CT-Guided Bronchoscopy With a Real-Time Electromagnetic Position Sensor," "A Comparison of Two Image Registration Methods." *Chest*, vol. 118, No. 6: 1783-1787, 2000.

Srivastava, S., "Computer-Aided Identification of Ovarian Cancer in Confocal Microendoscope Images," Department of Electrical and Computer Engineering, University of Arizona Graduate School, Thesis: 213pp, 2004.

Tearney et al., "Determination of the Refractive-Index of Highly Scattering Human Tissue by Optical Coherence Tomography." *Optics Letters*, vol. 20, No. 21: 2258-2260, 1995.

Tsai et al., "All-Optical Histology Using Ultrashort Laser Pulses." *Neuron* Cell Press, vol. 39: 27-41, Jul. 3, 2003.

Vakoc et al., "Comprehensive esophageal microscopy by using optical frequency-domain imaging (with video)." *Gastrointestinal Endoscopy*, vol. 65, No. 6: 898-905, 2007.

Wang et al., "Deep Reactive Ion Etching of Silicon Using an Aluminum Etching Mask." *Proceedings of SPIE*, vol. 4876: 633-640, 2003.

Wilson et al., "Optical Reflectance and Transmittance of Tissues: Principles and Applications." *IEEE Journal of Quantum Electronics*, vol. 26, No. 12: 2186-2199, Dec. 1990.

Xu et al., "3D Motion Tracking of pulmonary lesions using CT fluoroscopy images for robotically assisted lung biopsy." *Proceedings of SPIE*, vol. 5367: 394-402, 2004.

Yamada et al., "Characteristics of a Hemispherical Microlens for Coupling Between a Semiconductor Laser and Single-Mode Fiber." *IEEE J. Quant. Electron*, vol. QE-16, No. 10: 1067-1072, Oct. 1980.

Yamamoto et al., "Total enteroscopy with a nonsurgical steerable double-balloon method." *Gastrointestinal Endoscopy* vol. 53, No. 2: 216-220, Feb. 2001. Abstract only.

Yang et al., "High speed, wide velocity dynamic range Doppler optical coherence tomography (Part I): System design, signal processing, and performance." *Optics Express*, vol. 11, No. 7: 794-809, Apr. 7, 2003.

Yang et al., "Micromachined array tip for multifocus fiber-based optical coherence tomography." *Optics Letters*, vol. 29, No. 15: 1754-1756, 2004.

Yelin et al., "Double-clad fiber for endoscopy." *Optics Letters*, vol. 29, No. 20: 2408-2410, Oct. 15, 2004.

Yelin et al., "Three-dimensional miniature endoscopy." *NATURE* vol. 443: 765 plus supplemental information, Oct. 19, 2006. <www.nature.com/nature/journal/v443/n7113/extref/443765a-s2.doc>.

Yoon et al., "Analysis of Electro Active Polymer Bending: A Component in a Low Cost Ultrathin Scanning Endoscope." *Sensors and Actuators A—Physical*: pp. 1-26, Submitted Jan. 13, 2006, Published Jul. 2006.

Yun et al., "Comprehensive volumetric optical microscopy in vivo." *NATURE MEDICINE* vol. 12, No. 12: 1429-1433, Dec. 2006.

Yun et al., "Motion artifacts in optical coherence tomography with frequency-domain ranging." *Optics Express* vol. 12, No. 13: 2977-2998, Jun. 28, 2004.

Zhang et al., "In vivo blood flow imaging by a swept laser source based Fourier domain optical Doppler tomography." *Optics Express* vol. 13, No. 19: 7449-7457, Sep. 19, 2005.

Zipfel et al., "Live tissue intrinsic emission microscopy using multiphoton-excited native fluorescence and second harmonic generation." *PNAS* vol. 100, No. 12: 7075-7080, Jun. 10, 2003. Available at <www.pnas.org/cgi/doi/10.1073/pnas.0832308100>.

N.a., "NASA-Inspired Shape-Sensing Fibers Enable Minimally Invasive Surgery." NASA Tech Briefs vol. 32, No. 2: 12, 14, Feb. 2008.

N. a., "NANO™ SU-8 2000 Negative Tone Photoresist Formulations 2002-2025." Micro-Chem: 5pp, © 2001.

Barhoum et al., "Optical modeling of an ultrathin scanning fiber endoscope, a preliminary study of confocal versus non-confocal detection." *Optics Express*, vol. 13, No. 19: 7548-7562, Sep. 19, 2005.

(56) References Cited

OTHER PUBLICATIONS

Barnard et al., "Mode Transforming Properties of Tapered Single-mode Fiber Microlens." *Appl. Opt.* vol. 32, No. 12: 2090-2094, Apr. 20, 1993.

Barnard et al., "Single-mode Fiber Microlens with Controllable Spot Size." *Appl. Opt.* vol. 30, No. 15: 1958-1962, May 20, 1991.

Bird et al., "Two-photon fluorescence endoscopy with a micro-optic scanning head." *Optics Letters*, vol. 28, No. 17: 1552-1554, 2003.

Borreman et al., "Fabrication of Polymeric Multimode Waveguides and Devices in SU-8 Photoresist Using Selective Polymerization." *Proceedings Symposium IEEE/LEOS* Benelux Chapter, Amsterdam: pp. 83-86, 2002.

Brown et al., "Recognising Panoramas." *Proceedings of the Ninth IEEE International Conference on Computer Vision* 8pp., Apr. 2003.

Brunetaud et al., "Lasers in Digestive Endoscopy." *Journal of Biomedical Optics* vol. 2, No. 1: 42-52, Jan. 1997.

Chen et al., "Dispersion management up to the third order for real-time optical coherence tomography involving a phase or frequency modulator." *Optics Express* vol. 12, No. 24: 5968-5978, 2004.

Chen et al., "Optical Doppler tomographic imaging of fluid flow velocity in highly scattering media." *Optics Letters*, vol. 22, No. 1: 64-66, 1997.

Clark et al., "Fiber delivery of femtosecond pulses from a Ti:sapphire laser." *Optics Letters*, vol. 26, No. 17: 1320-1322, 2001.

Deschamps et al., "Automatic construction of minimal paths in 3D images: An application to virtual endoscopy." *CARS'99*—H.U. Lemke, M.W. Vannier, K. Inamura & A.G. Fannan (Editors) Elsevier Science B.V.: 151-155, 1999.

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Drexler et al., "In vivo ultrahigh-resolution optical coherence tomography." *Optics Letters*, vol. 24, No. 17: 1221-1223, 1999.

Finci et al., "Tandem balloon catheter for coronary angioplasty." *Catheter Cardiovascular Diagnosis* vol. 12, No. 6: 421-425, 1986. 2pp Abstract.

Flusberg et al., "In vivo brain imaging using a portable 3.9 gram two-photon fluorescence microendoscope." *Optics Letters*, vol. 30, No. 17: 2272-2274. 2005.

Fu et al., "Nonlinear optical microscopy based on double-clad photonic crystal fibers." *Optics Express* vol. 13, No. 14: 5528-5534 + supplemental page, 2005.

Göbel et al., "Miniaturized two-photon microscope based on a flexible coherent fiber bundle and a gradient-index lens objective." *Optics Letters*, vol. 29, No. 21: 2521-2523, 2004.

Helmchen et al., "A Miniature Head-Mounted Two-Photon Microscope: High Resolution Brain Imaging in Freely Moving Animals." *Neuron* vol. 31: 903-912, Sep. 27, 2001.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging 2003*, vol. 5031: 80-89, 2003.

Huang et al., "Optical Coherence Tomography." *Science* vol. 254, Issue 5035: 1178-1181, 1991.

Huber et al., "Amplified, frequency swept lasers for frequency domain reflectometry and OCT imaging: design and scaling principles." *Optics Express* vol. 13, No. 9: 3513-3528, May 2, 2005.

Jung et al., "Multiphoton endoscopy." *Optics Letters*, vol. 28, No. 11: 902-904, 2003.

Kiesslich et al., "Diagnosing *Helicobacter pylori* In Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lewis et al., "Scanned beam medical imager." *MOEMS Display and Imaging System II*, edited by Hakan Urey, David L. Dickensheets, Proceedings of SPIE, Bellingham, WA, vol. 5348: 40-51, 2004.

Lexer et al., "Dynamic coherent focus OCT with depth-independent transversal resolution." *Journal of Modern Optics* vol. 46, No. 3: 541-553, 1999.

Li et al., "Optical Coherence Tomography: Advanced Technology for the Endoscopic Imaging of Barrett's Esophagus" *Endoscopy*, vol. 32, No. 12: 921-930, 2000.

Liu et al., "3D Navigation for Endoscope by Magnetic Field." *Proceedings of SPIE*, vol. 4556 25-28, 2001.

Liu et al., "Rapid-scanning forward-imaging miniature endoscope for real-time optical coherence tomography." *Optics Letters*, vol. 29, No. 15: 1763-1765, 2004.

\* cited by examiner

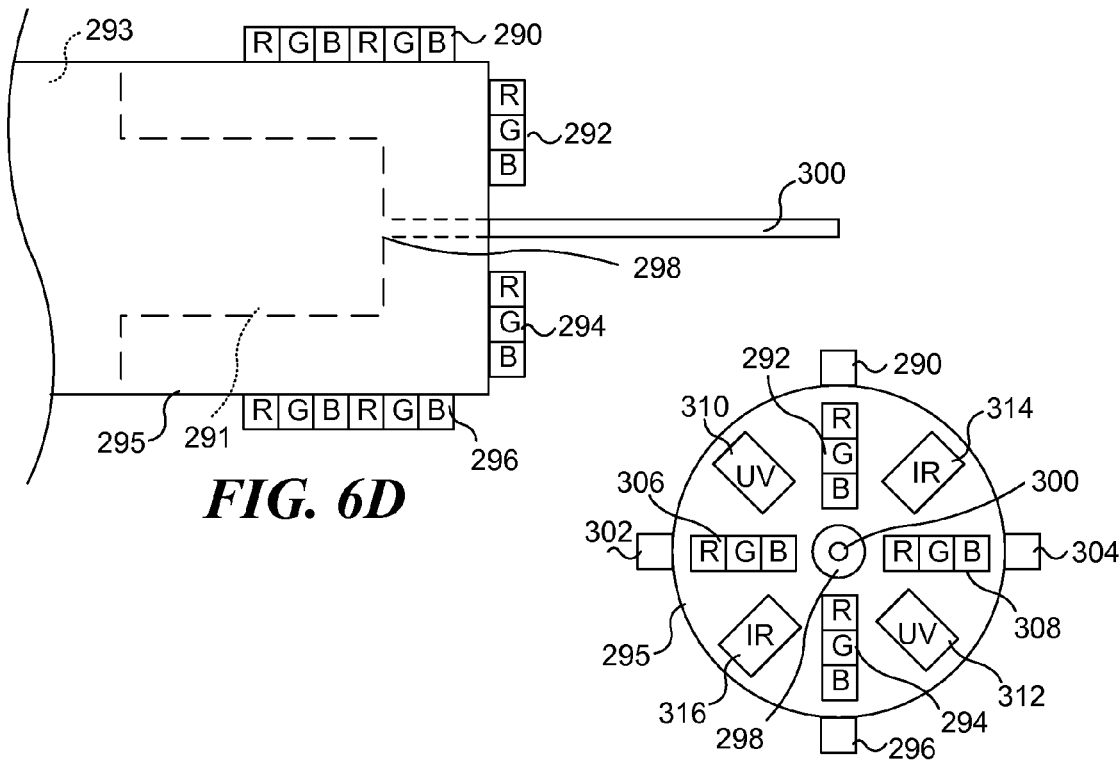
FIG. 6D
FIG. 6E
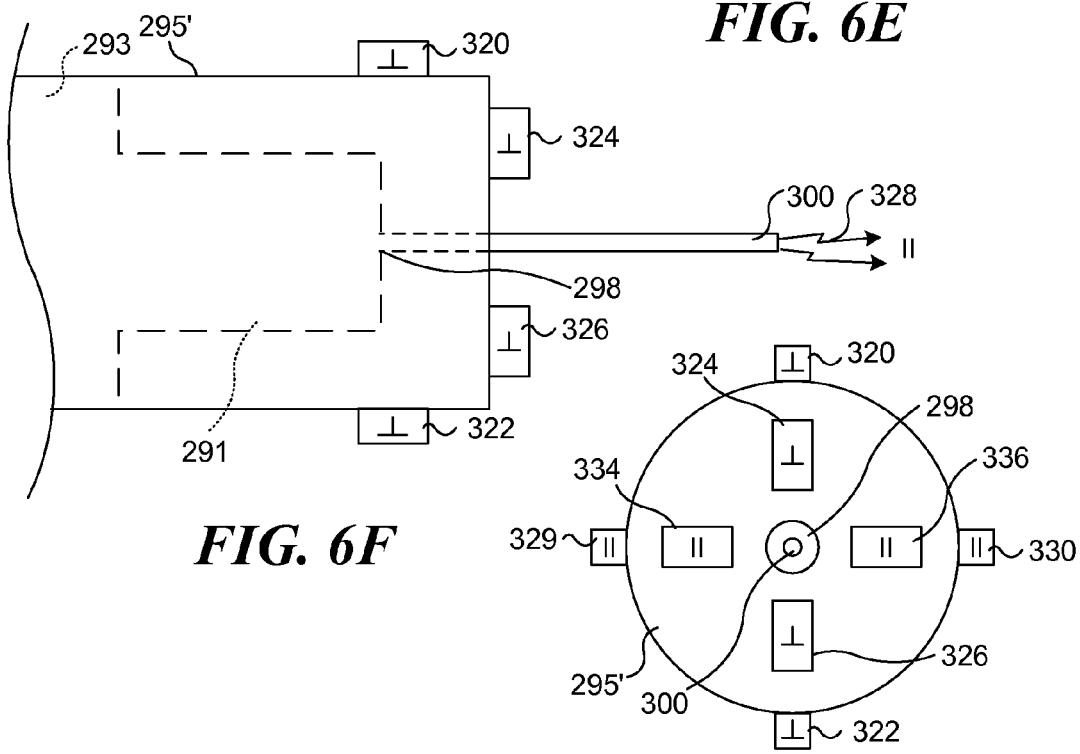
FIG. 6F
FIG. 6G

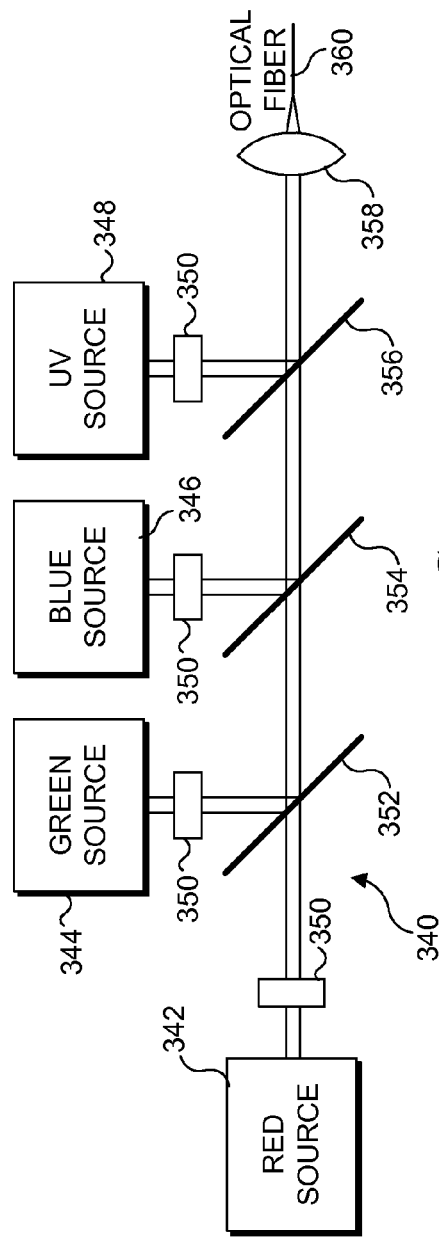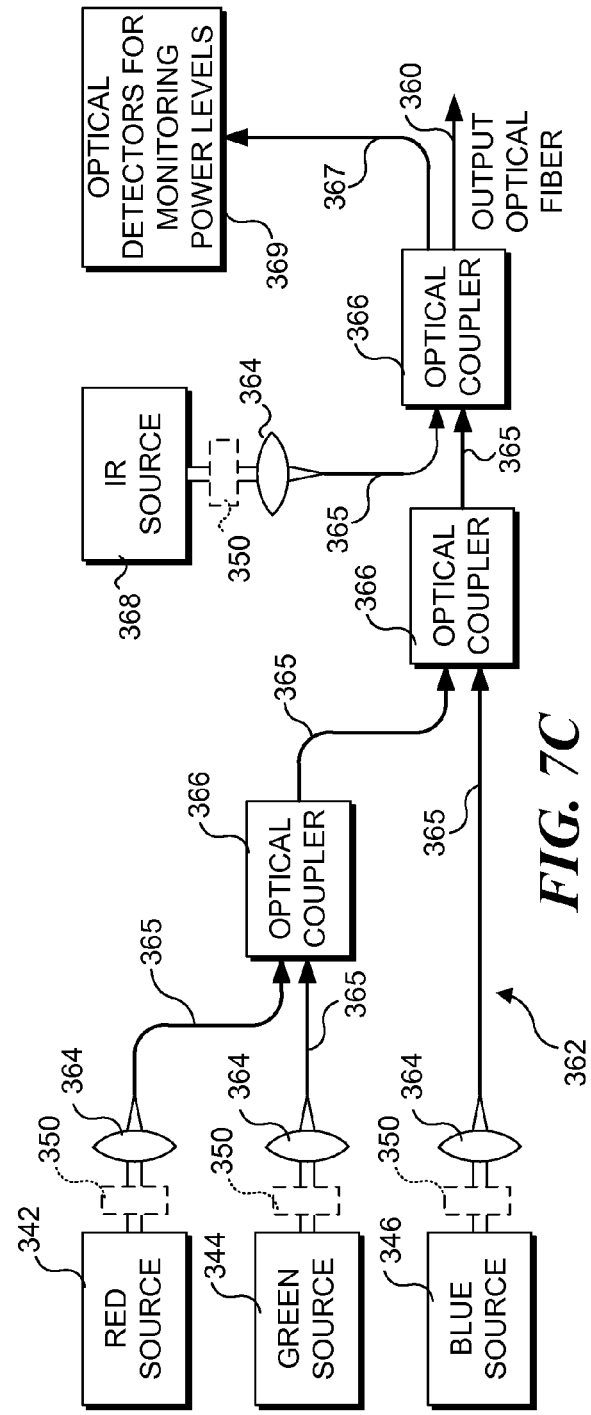
FIG. 7B
FIG. 7C

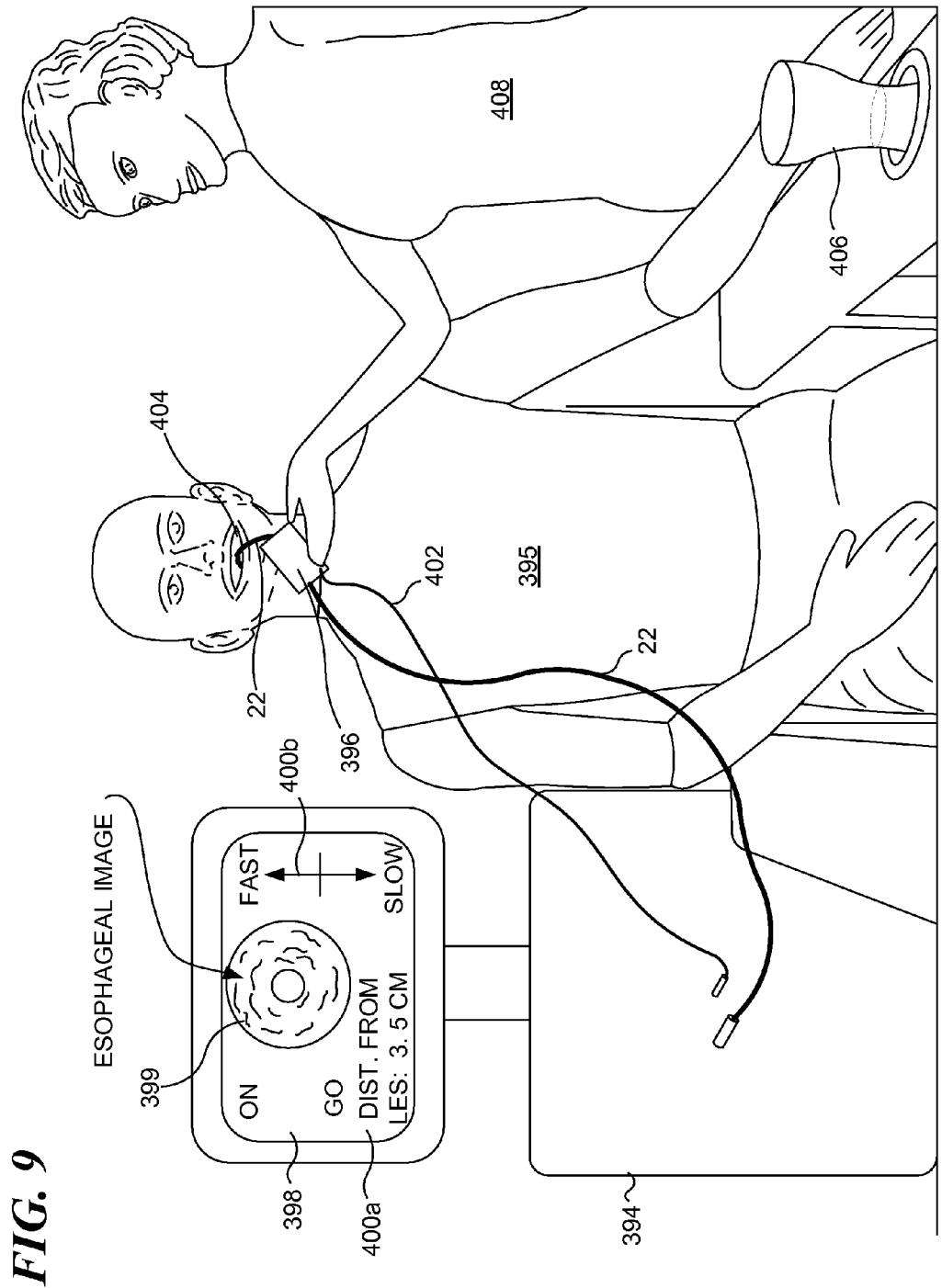

REPRESENTATION OF AN
EXEMPLARY ANALOG PATTERN

REPRESENTATION OF AN
EXEMPLARY DIGITAL PATTERN

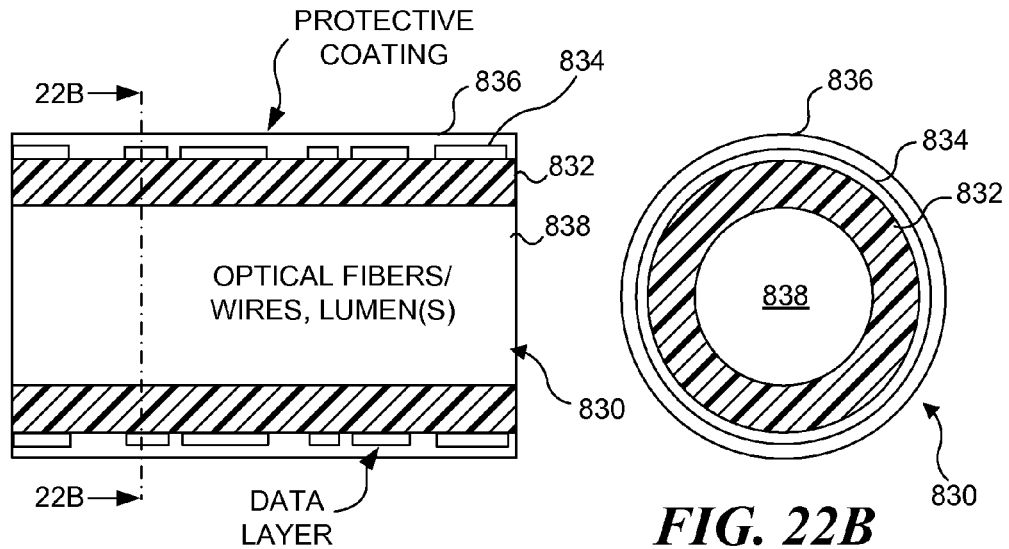
FIG. 22A
FIG. 22B
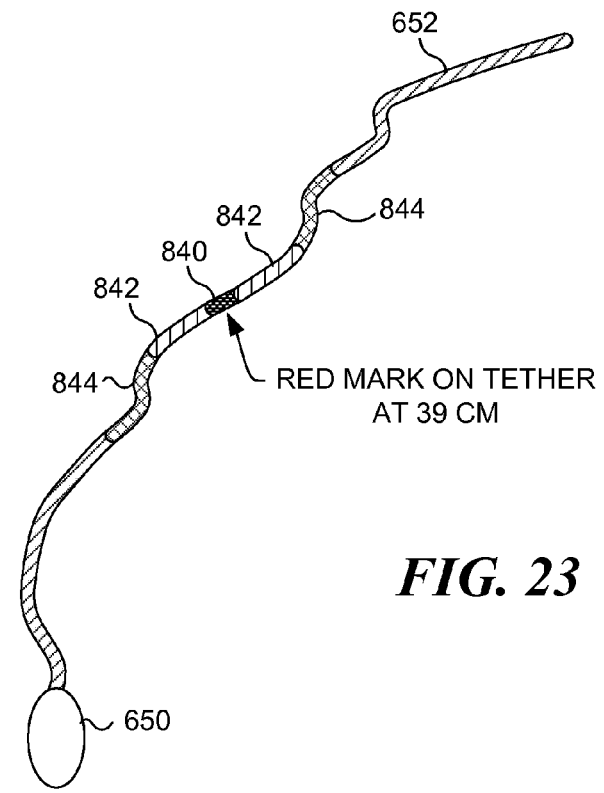
FIG. 23

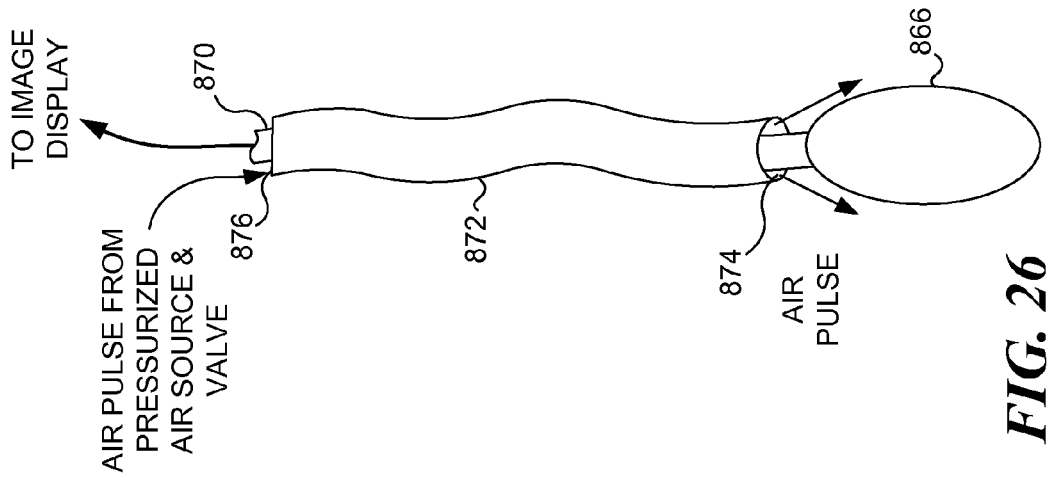
FIG. 26
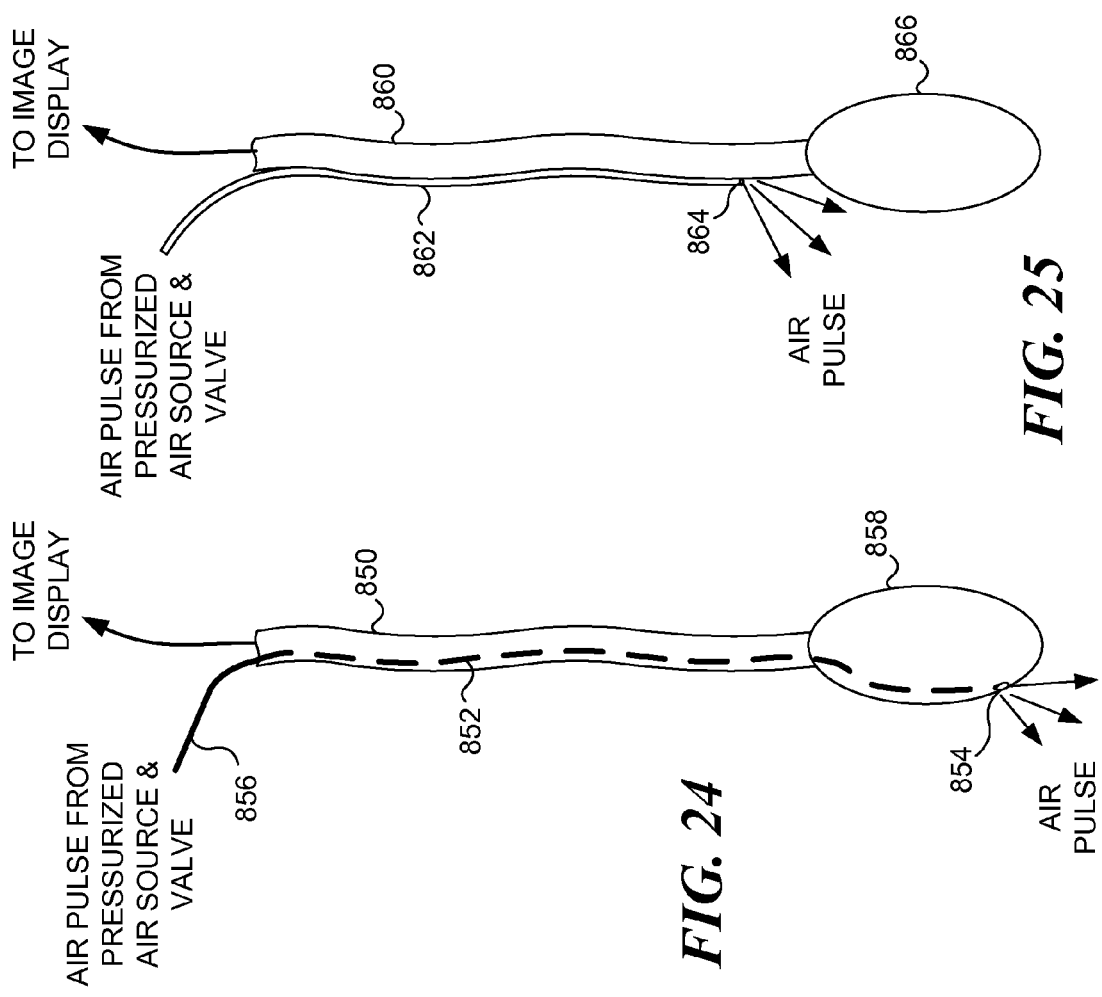
FIG. 25
FIG. 24

MONITORING DISPOSITION OF TETHERED CAPSULE ENDOSCOPE IN ESOPHAGUS

RELATED APPLICATIONS

This application is a continuation-in-part (CIP) of a patent application Ser. No. 11/069,826, filed on Feb. 28, 2005, now U.S. Pat. No. 7,530,948 the benefit of the filing date of which is hereby claimed under 35 U.S.C. §120.

BACKGROUND

Barrett's Esophagus (BE) is a condition of the esophagus that is pre-cancerous, a precursor to cancer of the esophagus. The standard practice for diagnosing Barrett's Esophagus uses a flexible endoscopy procedure, often with the esophageal lumen insufflated with air. A normal esophagus is usually light pink in color, while the stomach appears slightly darker pink. Barrett's Esophagus usually manifests itself as regions of slightly darker pink color above the lower esophageal sphincter (LES) that separates the stomach from the esophagus.

It is preferable to diagnose BE early, since this condition has been found to be a precursor of esophageal adenocarcinoma. Accordingly, it would be desirable to provide a general screening procedure for the condition, even though doing so would require evaluating the condition of the esophagus in millions of people with chronic heartburn and gastric reflux. However, Barrett's Esophagus and early stage cancers can occur without telltale symptoms, so mass screenings have been proposed as the only viable approach to identify the condition as early as possible to enable treatment and avoid the onset of or provide a curative therapy for the cancerous condition. Unfortunately, the numbers of people that are likely candidates for esophageal screening and the current cost associated with the practice of flexible endoscopy performed by a physician compared to the reimbursement associated with such mass screenings make this solution currently impractical because of the expense involved.

What is needed is a much more efficient and cost effective approach for identifying those people having Barrett's Esophagus. Only a doctor can perform an examination of the esophagus using a conventional flexible endoscope, and the procedure is thus relatively expensive. It would be preferable to develop a different scanning technique that need not be performed by a physician, but instead, can be performed by a trained medical technician or nurse. Indeed, it would also be desirable to automate the evaluation of images produced by imaging the internal surface of the esophagus just proximal of the LES so that the existence of Barrett's Esophagus can be automatically detected either in real time during the scanning operation or immediately thereafter.

To facilitate mass screenings of individuals who may be afflicted with Barrett's Esophagus, it would be desirable to employ a screening device that can readily be introduced into the esophagus, without invoking any gag reflex. Ideally, the scanning device should be embodied in a capsule-shaped housing so that it can simply be swallowed with a glass of water. Accordingly, the device must be sufficiently small in size to enable it to be swallowed by most patients. Further, although such a device might be reusable if properly sterilized, it may be desirable to employ a screening device that is sufficiently low in cost as to be disposable after a single use.

The above-noted earlier related application discloses an approach for monitoring a position in a person's esophagus of an endoscope that is well-suited for providing images that can be used to evaluate the condition of the esophagus and thereby detect BE. In this earlier approach, a tether attached to a capsule endoscope that includes an imaging device passes over a wheel that rotates as the capsule is moved axially within the esophagus, to enable the relative position of the capsule in the esophagus to be continually monitored. The axial position of the capsule is important so that the locations of regions, which may be of interest in images of the inner surface of the esophagus, can be identified and to enable the axial scaling of any panoramic images taken. However, the measurement of the axial position depends upon the frictional contact between the tether and the measurement wheel. There are three reasons why this method may not produce sufficiently accurate results. In this earlier described approach, the tether must be kept under tension, and the measurement technique relies on no-slip friction between the measurement wheel and the moving tether. Slippery saliva and mucus within the person's mouth and esophagus can adhere to the tether creating slippage between the measurement wheel that is rotated and the tether. In addition, the clinician performing the procedure may want to feel the progression of the tethered capsule scope as it passes through the lower esophageal sphincter and other parts of the esophagus, and the additional applied tension produced by the measurement wheel (which was disclosed as a pinch wheel) is likely to interfere with that feel. Similarly, the clinician may want to move the capsule scope up and down within the esophagus in a repeated manner, which will likely introduce measurement error in a mechanical system that is based on the friction between the measurement wheel and the tether. Any hysteresis in the measurement can be a further source of error.

Accordingly, a better technique for monitoring the axial position of the capsule scope is desired. The approach that is used should monitor the movement of the capsule by detecting the motion of the tether without actual contact between the tether and the axial position monitoring apparatus. The presence of saliva and mucus should have minimal impact on the monitoring technique used, and the feel as the capsule scope is moved up and down should be readily experienced by the clinician without interference from the apparatus used to monitor the position of the capsule.

SUMMARY

A scanning fiber endoscope (SFE) includes a scanning capsule having a scanning device and a tether coupled to the capsule for controlling a position of the scanning capsule within a body lumen. Since it is important to monitor at least a relative position of the scanning capsule without introducing errors as a result of bodily fluids that may coat the tether and to avoid interfering with the "feel" of a clinician who is controlling the position of the scanning capsule within the body lumen, a novel method has been developed to achieve this function. The method thus enables monitoring a relative position of a scanning capsule within a body lumen. The tether that has a distal end coupled to the capsule extends externally of the body lumen and carries a scan signal produced in the scanning capsule that is useful to produce an image of an interior surface of the body lumen. The method includes the step of providing an indicia along an axial length of at least a portion of the tether, which is indicative of a position. Using a sensor that responds to the indicia without requiring physical contact with the tether, the indicia are automatically sensed, producing a position signal indicative of the position of the tether and thus, of the disposition of the scanning capsule axially within the body lumen.

At least one non-numeric visible reference mark can be provided on the tether to indicate an expected reference position. This reference mark can thus enable a user to manually position the capsule at about a desired location based upon the visual indication provided by the non-numeric visible reference mark on the tether. While not a requirement, the body lumen can comprise an esophagus. In this case, the expected reference position might correspond to a position on the tether that should indicate when the capsule is expected to be disposed at about a gastroesophageal junction in the esophagus. A plurality of additional non-numeric visible marks can also be provided both distally and proximally of the at least one non-numeric visible reference mark, to visually indicate positions or distances on either side of the expected reference position.

In one exemplary embodiment, the step of automatically sensing the indicia can include the step of using a magnetic sensor for producing the position signal in response to a varying parameter of a magnetic field that is produced by the indicia on the tether. The position signal that is produced can be either a digital position signal or an analog position signal, both of which are indicative of a current position along the axial length of the tether, adjacent to the magnetic sensor.

In a different exemplary embodiment, an optical sensor can be used for producing the position signal in response to an optical parameter of the indicia that varies along the axial length of the tether. Again, the step of producing the position signal can produce either a digital position signal or an analog position signal, either of which is indicative of a current position along the axial length of the tether, adjacent to the optical sensor. The indicia can comprise an optical code that produces the position signal in response to at least one parameter selected from a group of parameters. These parameters include: a color of the optical code that is sensed by the optical sensor; a digital value indicated by the optical code; an intensity of light reflected from the optical code compared to an intensity of light reflected from a background area; a pattern of the optical code that conveys digital information; a relative size of markings comprising the optical code; a shape of the markings comprising the optical code; a scattering of light by the optical code compared to a scattering of light from the background area; and a wavelength of light reflected by or absorbed by the optical code.

In a further alternative exemplary embodiment, an additional sensor can be provided to monitor the indicia on the tether, to increase a resolution with which the relative position of the capsule in the body lumen is determined.

The step of providing the indicia can include applying the indicia by either affixing the indicia to the tether as a longitudinally extending tape, or by applying the indicia to the tether as a longitudinally extending coating. Optionally, the indicia can be protected with a protective coating that is applied over the indicia. In some exemplary embodiments, the method can include the step of providing a scraper for gently wiping bodily fluids from the tether as the tether is withdrawn from the body lumen, and before the tether passes the position sensor.

In some applications, the exemplary method includes the step of determining a reference position for the capsule within the body lumen relative to which the indicia are used, to determine the position of the capsule within the body lumen. For example, the reference position can be determined by moving the capsule to a known position within the body lumen based upon the images of an interior surface of the body lumen. The disposition of the capsule at the known position thus represents the reference position that is then used to determine subsequent positions of the capsule as the tether is used to move the capsule within the body lumen.

Another aspect of the present technology is directed to exemplary apparatus for measuring a relative position in a body lumen of a capsule used for scanning an inner surface of the body lumen to produce images. The apparatus includes a tether and a non-contact position sensor that are generally consistent with the method discussed above.

Yet another aspect of this technology is directed to an exemplary method for measuring an axial extent of a region of interest within a body lumen in regard to images produced by a scanning device in a capsule that is coupled to a tether having a proximal end that extends outside the body lumen and is used to move the capsule. The method includes the step of monitoring the distance that the capsule is moved through the body lumen with the tether by monitoring movement of the tether past a sensor disposed outside the body lumen. Successive images of an internal surface of the body lumen are captured as the tether is used to move the capsule axially through the body lumen. A region of interest on the internal surface of the body lumen is detected in the successive images, and based upon a first position of the capsule within the body lumen corresponding to an axial start and a second position corresponding to an axial end of the region of interest, the axial extent of the region of interest is measured, with reference to the distance between the first position and the second position that the tether moves the capsule. Also disclosed below is an apparatus for carrying out this distance measuring function.

Still another aspect of the technology is directed to a method for use with a capsule having a scanner for imaging an inner surface of an esophagus, where the capsule is coupled to a tether for moving the capsule within the esophagus and through a gastroesophageal junction. In this method (and in regard to corresponding apparatus) using the tether, the capsule is moved within the esophagus to a position adjacent to the gastroesophageal junction. A pulse of pressurized fluid is then delivered to a region adjacent to the capsule. The pulse of pressurized fluid causes a lower portion of the esophagus to autonomously be distended, thereby facilitating movement of the capsule through the gastroesophageal junction and into and out of a stomach of a patient, while a scanner in the capsule is used for imaging the inner surface of the esophagus.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 7A:
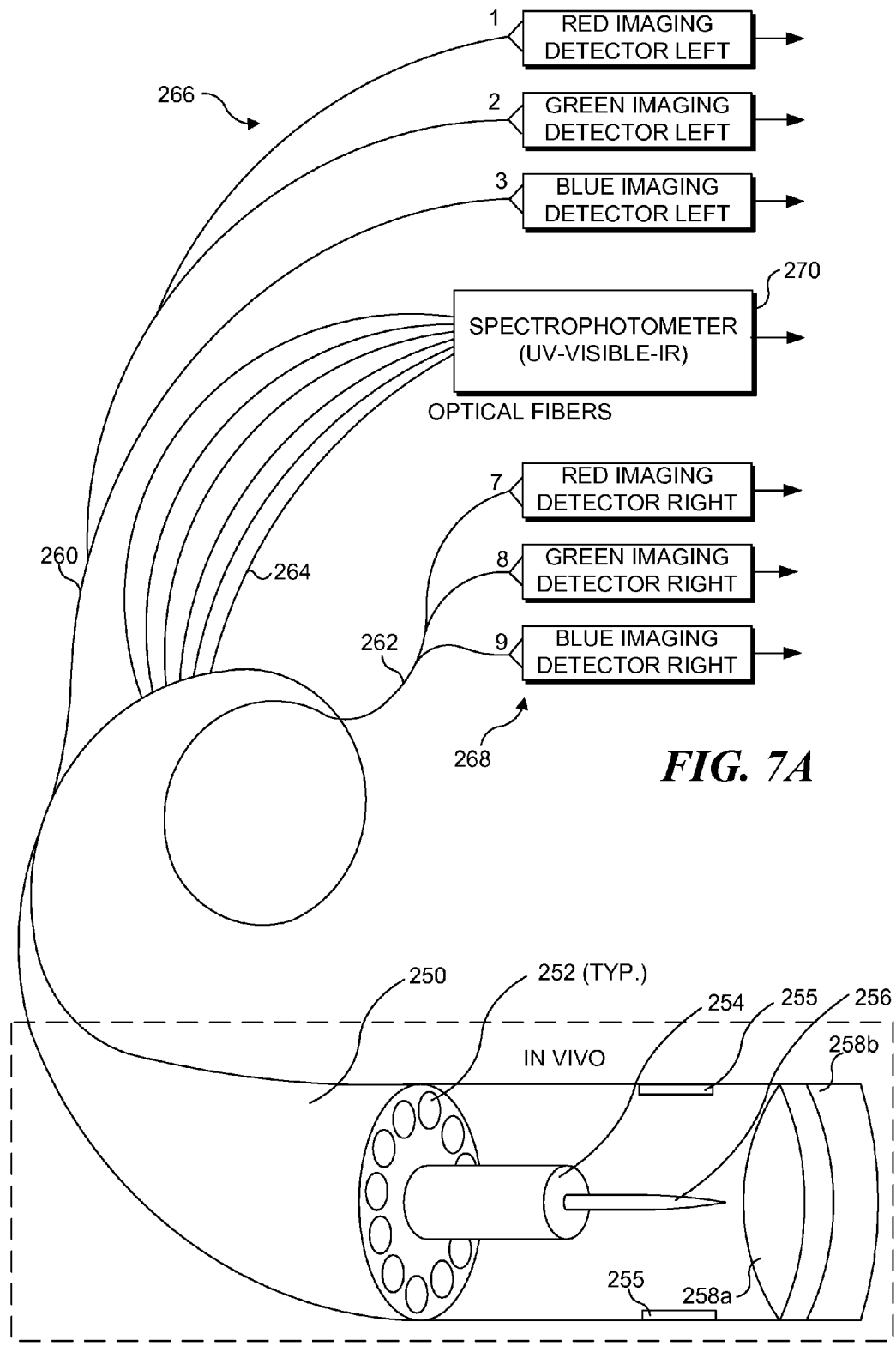
Figure 8A:
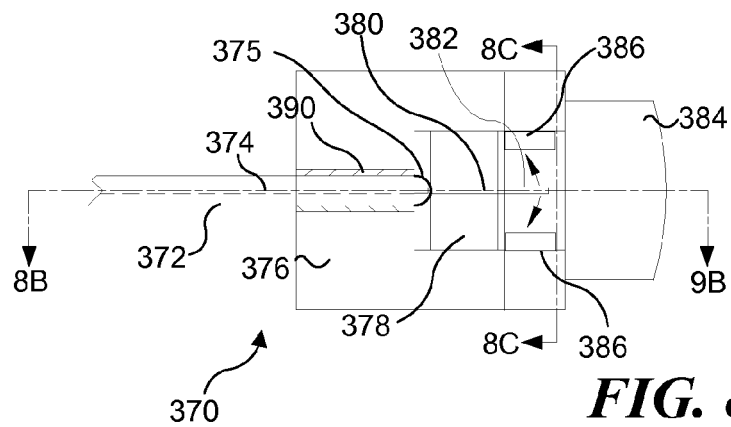
Figure 8B:
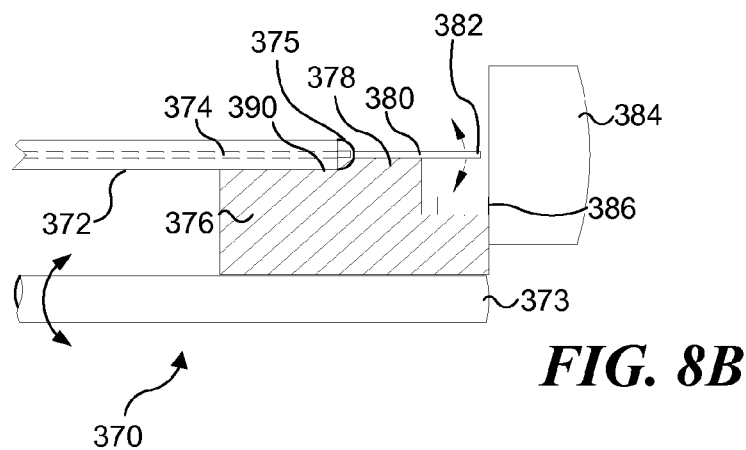
Figure 8C:
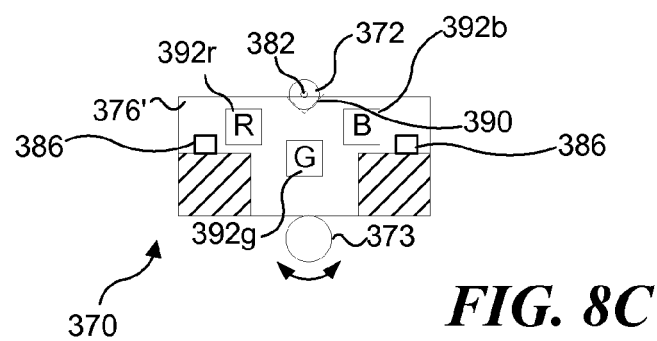
Figure 8D:
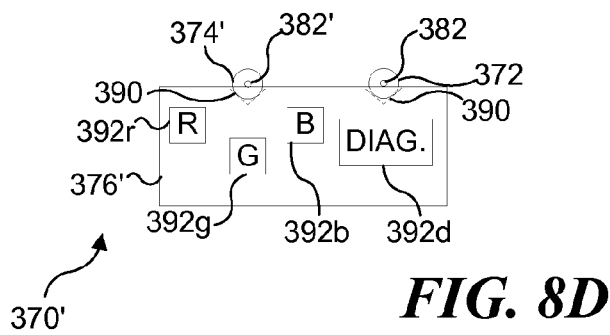
Figure 10:
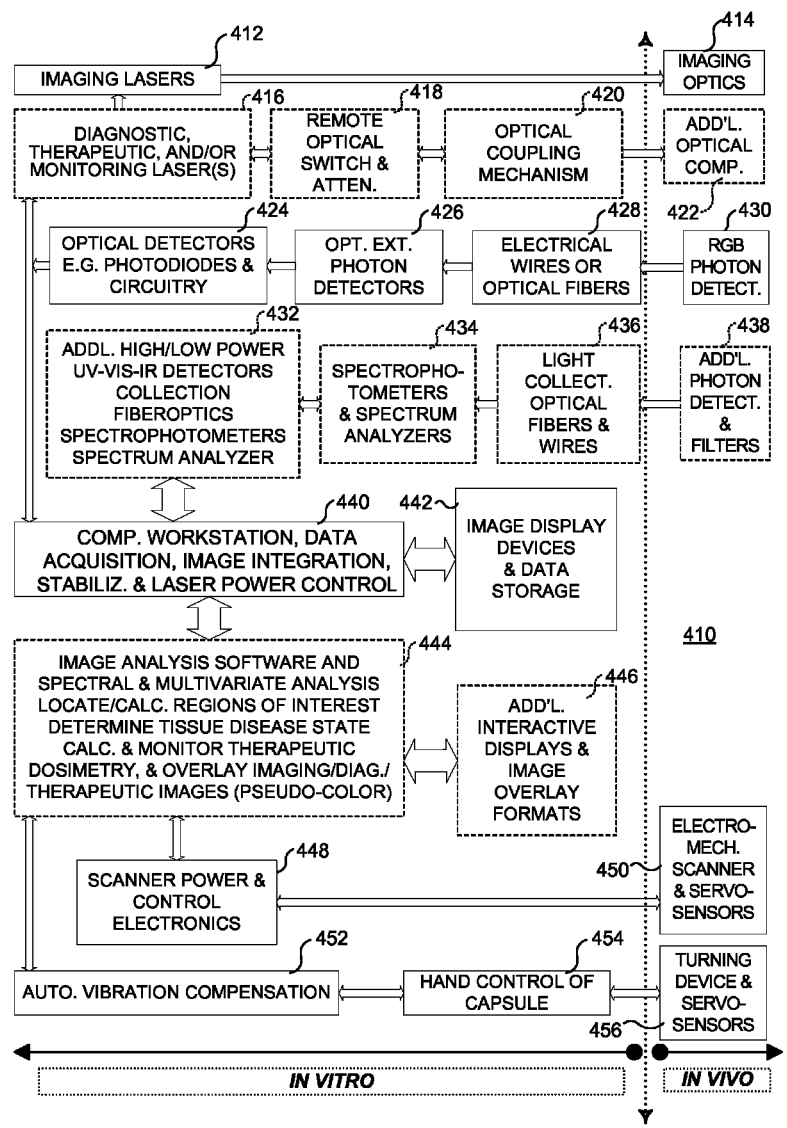
Figure 11A:
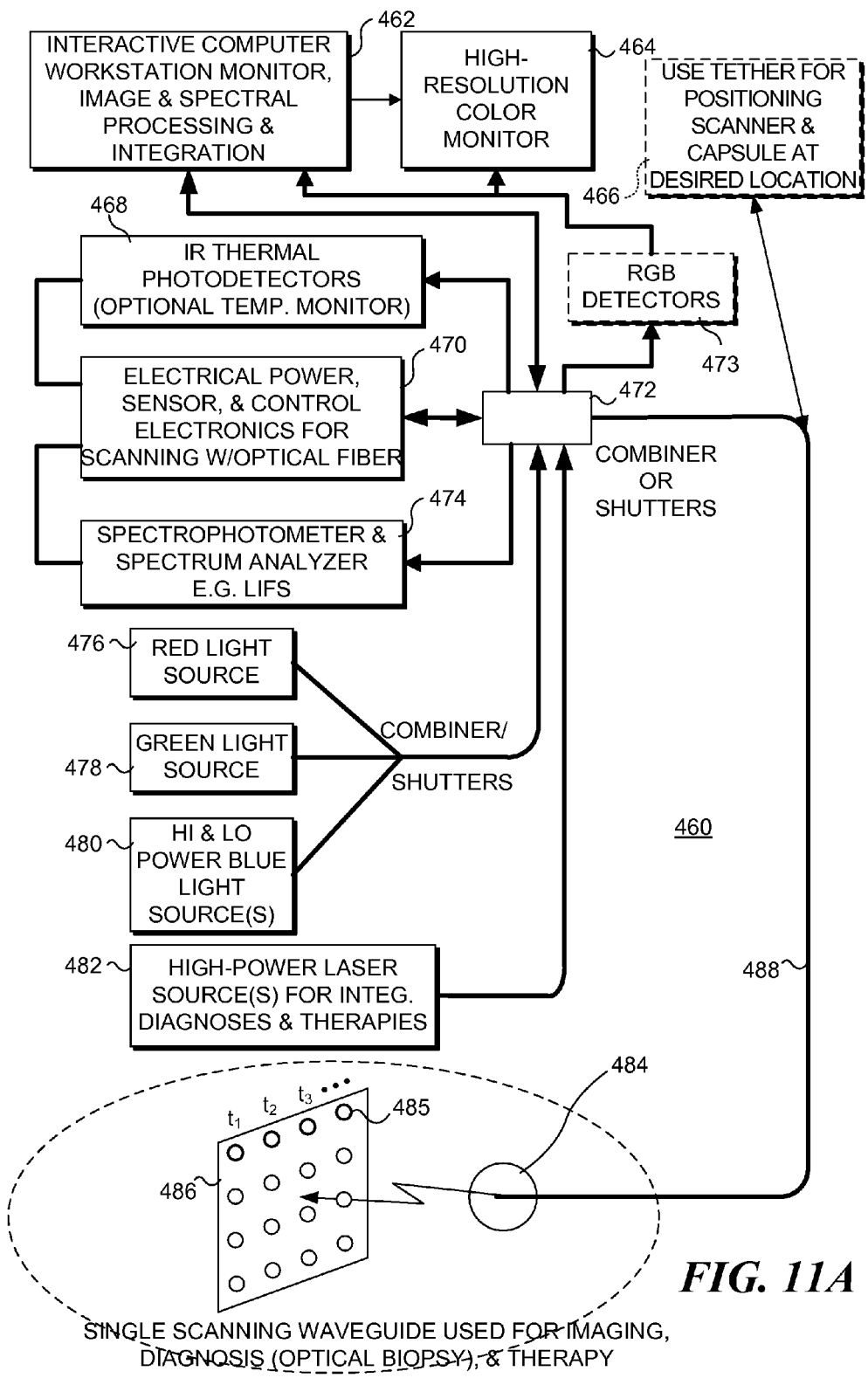
Figure 11B:
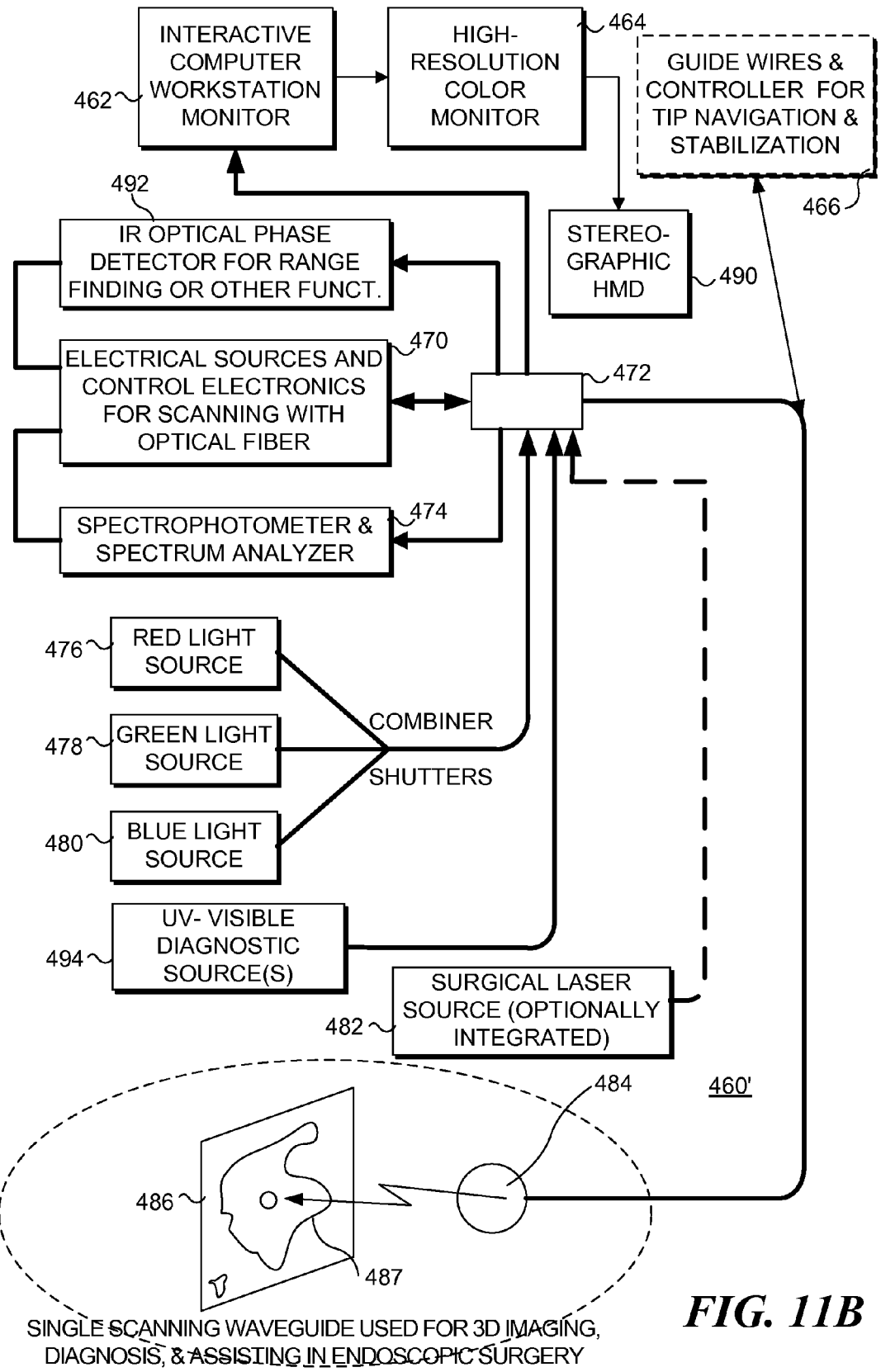
Figure 12:
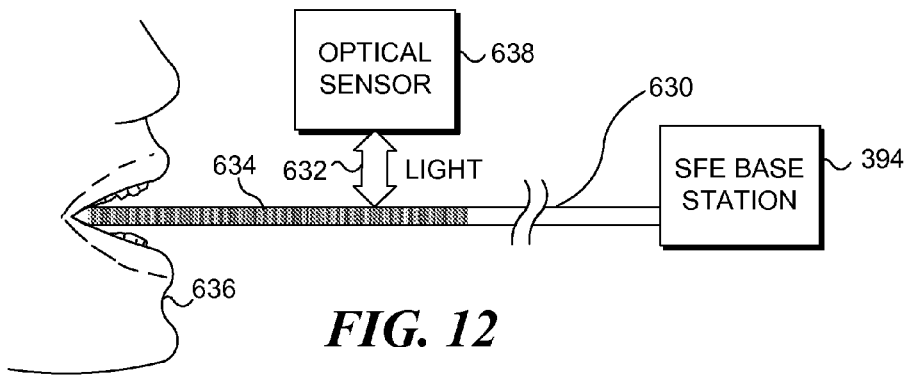
Figure 13:
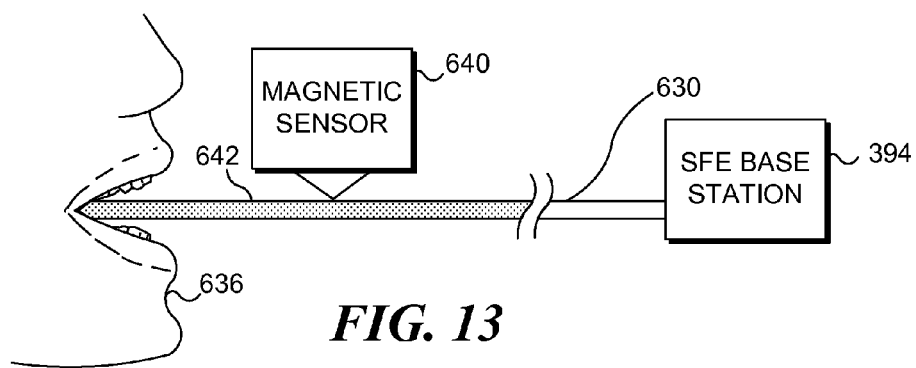
Figure 14:
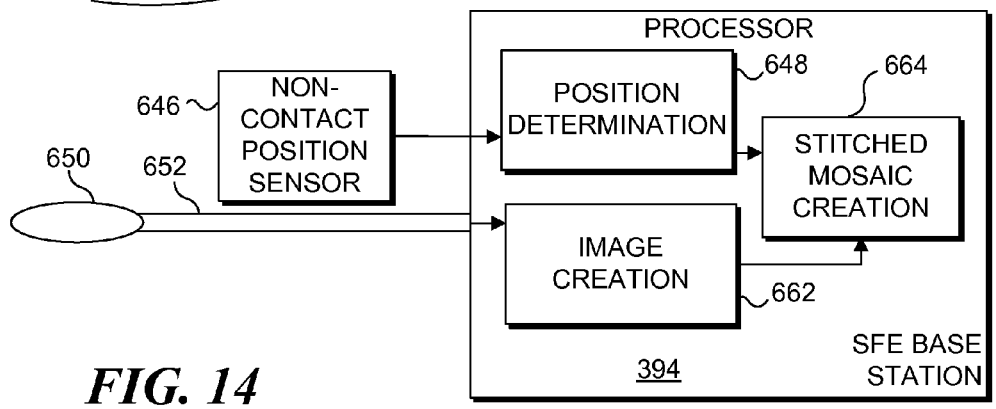
Figure 15:
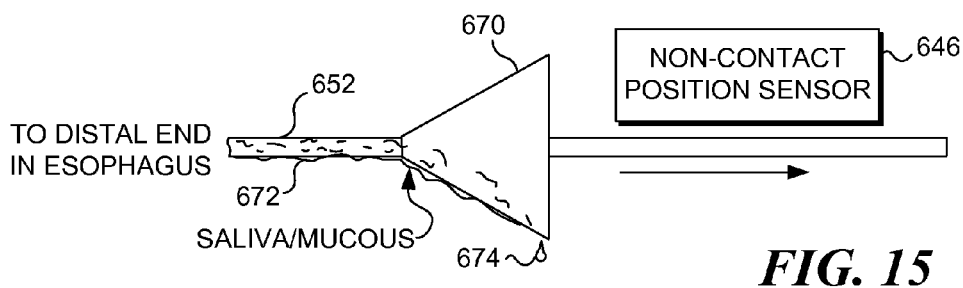
Figure 16:
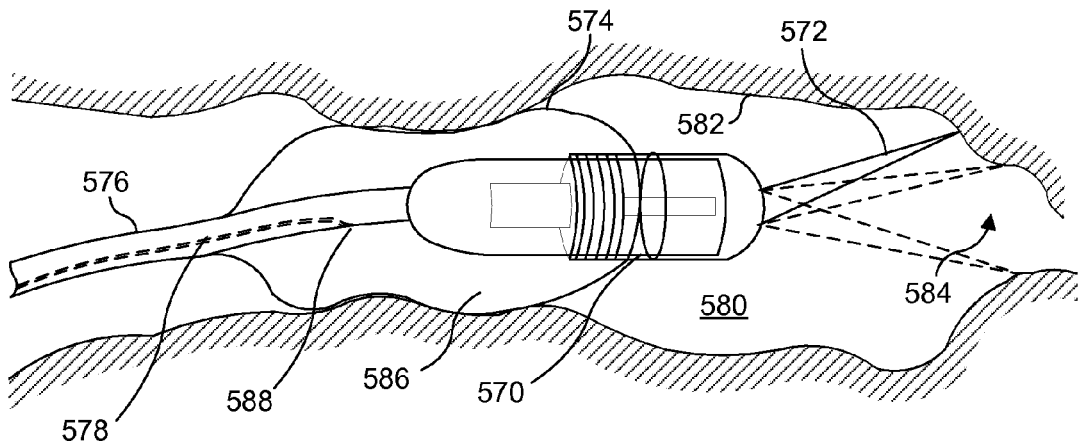
Figure 17:
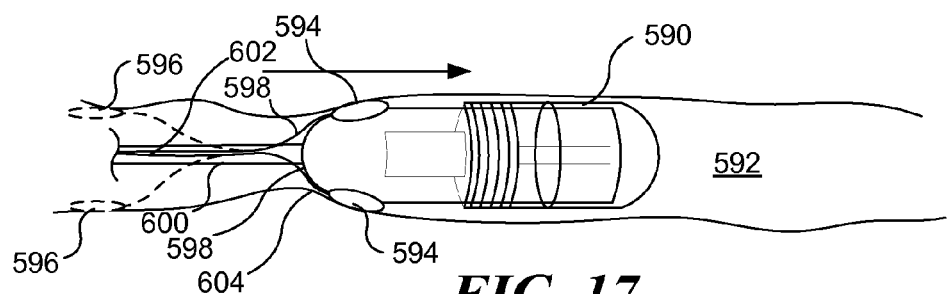
Figure 18:
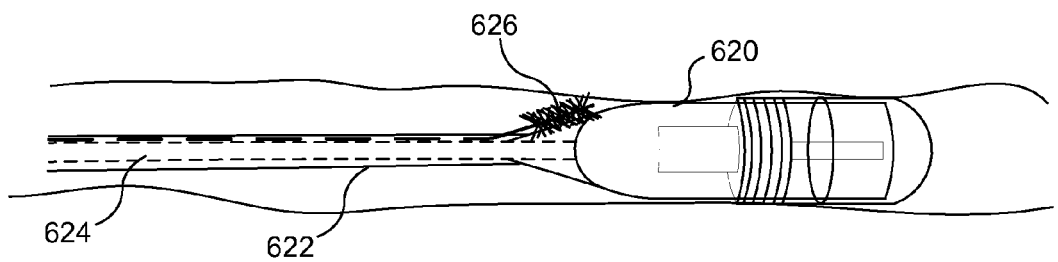
Figure 19:
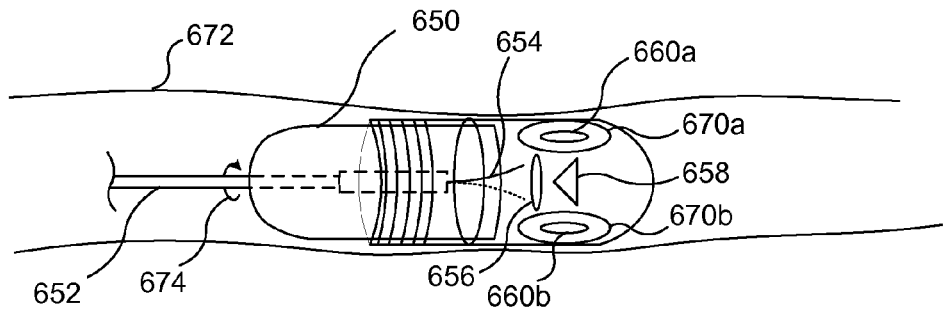
Figure 20A:
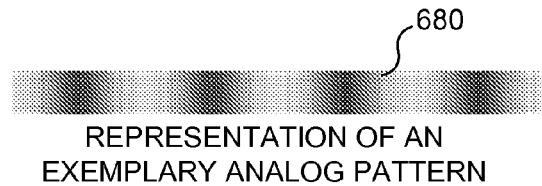
Figure 20B:
Figure 21:
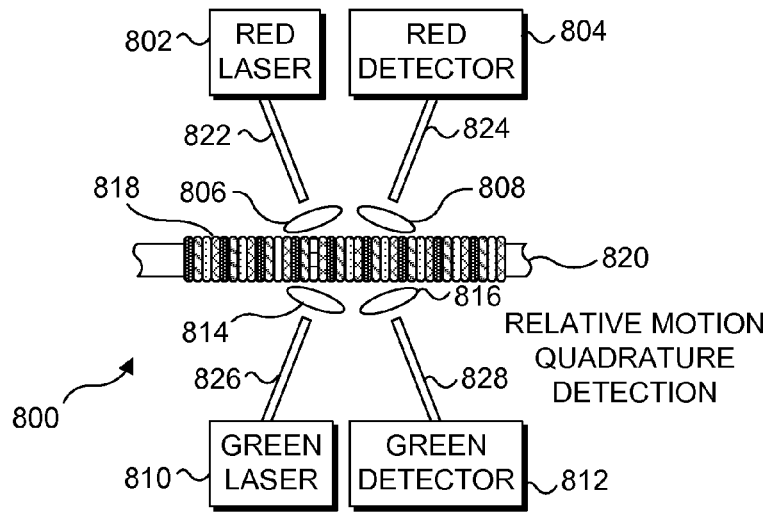

FIGS. 6D and 6E schematically illustrate a scanner having distal photon red, green, blue (RGB) filtration and detection using stereo-paired geometry and the ability to subtract background scatter using forward and side-facing spatial arrangements of detectors, respectively shown in a side elevational view and in an end view;

FIGS. 6F and 6G schematically illustrate a scanner having distal photon polarized filtration and detection using stereo-paired geometry and the ability to enhance signals from superficial tissue on the inner surface of a lumen, using forward and side-facing spatial arrangements of detectors, respectively shown in a side elevational view and in an end view;

FIG. 7A is a schematic diagram showing the configuration of a scanner with distal optical fiber position sensors and proximally disposed photon detectors with proximal optical fiber light collectors that are capable of pseudo-stereo image acquisition;

FIG. 7B is a schematic diagram of an optical fiber scanning system for use with the present invention, which employs radiation from visible and UV laser sources combined with dichroic filters;

FIG. 7C is a schematic diagram of an optical fiber system for use with the present invention, which employs radiation from visible and IR laser sources combined with fiber optic combiners connected in series;

FIGS. 8A, 8B, and 8C respectively illustrate a top plan view, a side elevational cross-sectional view taken along section line 8B-8B in FIG. 8A, and an end view taken along section line 8C-8C in FIG. 8A, of an embodiment of a thin film, microelectromechanical (MEMS) system scanner that is usable in the present invention;

FIG. 8D illustrates an end elevational view of another embodiment that includes a pair of thin film parallel cantilevers for illumination of an interior surface of a lumen;

FIG. 9 illustrates a medical practitioner using the present invention to carry out automated scanning and diagnostic evaluation of a patient's esophagus, such as might occur during mass screenings of the general population for BE;

FIG. 10 is a block diagram illustrating the functional input and output components of an optical fiber scanner system for use with the present invention;

FIG. 11A is a functional block diagram of an integrated cancer imaging, screening, and biopsy system, with optical therapy delivery and monitoring capabilities using a capsule and scanner in accord with the present invention;

FIG. 11B is a functional block diagram of an integrated cancer imaging and diagnostic system, with stereograph surgical support and display capabilities using a capsule and scanner in accord with the present invention;

FIG. 12 is a schematic side elevational view illustrating an exemplary embodiment of a non-contact optical sensor that is used to measure a position of a tether and thus, the position of a scanning capsule that is coupled to the tether, within an esophagus of a patient, in response to optical indicia provided on the tether;

FIG. 13 is a schematic side elevational view illustrating an exemplary embodiment of a non-contact magnetic sensor that is used to measure a position of a tether and a scanning capsule within an esophagus of a patient, in response to magnetic indicia provided on the tether;

FIG. 14 is an exemplary schematic block diagram illustrating how the tether and the non-contact sensor that monitors the disposition of a capsule are coupled to functional components of a scanning fiber endoscope (SFE) base station;

FIG. 15 is a schematic elevational view of a portion of a tether, showing how an exemplary elastomeric scraper is used to wipe saliva and mucous from the tether as the tether is pulled from the esophagus of a patient, past a non-contact sensor that measures the position of the tether and capsule within the esophagus;

FIG. 16 is a schematic view of a capsule having a balloon attached, wherein the balloon is shown inflated in a lumen;

FIG. 17 is a schematic view of a capsule having electrodes to cause muscle tissue peristalsis that advances the capsule through a lumen;

FIG. 18 is a schematic view of a capsule having a tether that includes an annular channel through which a biopsy instrument, such as a cytological brush is advanced to take a biopsy of tissue from an inner surface of a lumen;

FIG. 19 is a schematic view of a capsule having a pyramidal-shaped mirror for simultaneously laterally imaging opposite inner surfaces of a lumen, showing how the tether can be used to rotate the capsule as needed to encompass a full view of the inner surface of a lumen;

FIG. 20A is a representation of an exemplary analog pattern applied to a tether to enable a non-contact sensor to determine a position of the tether and the attached capsule within an esophagus, based upon the analog signal produced, for example, by an optical sensor responding to the analog pattern;

FIG. 20B is a representation of an exemplary digital pattern applied to a tether to enable a non-contact sensor to determine a position of the tether and the attached capsule within an esophagus, based upon the digital signal produced, for example, by an optical sensor responding to the digital pattern;

FIG. 21 is a schematic view of an exemplary embodiment that includes dual optical sensors with lenses, for responding to a dual color optical pattern applied to a tether, to determine the relative position of the tether/capsule in a body lumen such as the esophagus;

FIG. 22A is a schematic cut away view of an exemplary tether with data applied on a data layer protected by a transparent coating;

FIG. 22B is a transverse cross-sectional view of the tether, data layer, and protective coating, taken along section line 22B of FIG. 22A;

FIG. 23 is an exemplary view of a tether provided with visible markings that indicate the expected portion of the tether that must be inserted into an esophagus so that the capsule will be disposed at about the gastroesophageal junction where the esophagus is joined to the stomach;

FIG. 24 is a schematic illustration of an exemplary embodiment that includes a passage to convey a pulse of pressurized air (or other fluid) to a point proximal the capsule, to autonomously cause the esophagus to distend;

FIG. 25 is a schematic illustration of another exemplary embodiment that includes an adjacent external tube used to convey a pulse of pressurized air (or other fluid) to a point proximal the capsule; and FIG. 26 is a schematic illustration of still another exemplary embodiment that an external tube that is slid over the tether and is used to convey a pulse of pressurized air (or other fluid) to a point proximal the capsule.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Exemplary Application of Scanning Capsule

Although an exemplary embodiment of a scanning capsule was initially conceived as a solution for providing relatively low cost mass screening of the general population to detect BE without requiring interaction by a physician, it will be apparent that this embodiment is also generally applicable for use in scanning, providing diagnoses, rendering therapy, and monitoring the status of therapy thus delivered to an inner surface of almost any lumen in a patient's body. Accordingly, although the following discussion often emphasizes the application of the scanning capsule in the detection of BE, it is not intended that the application of this device be in any way limited to that specific application.

Figure 1A:
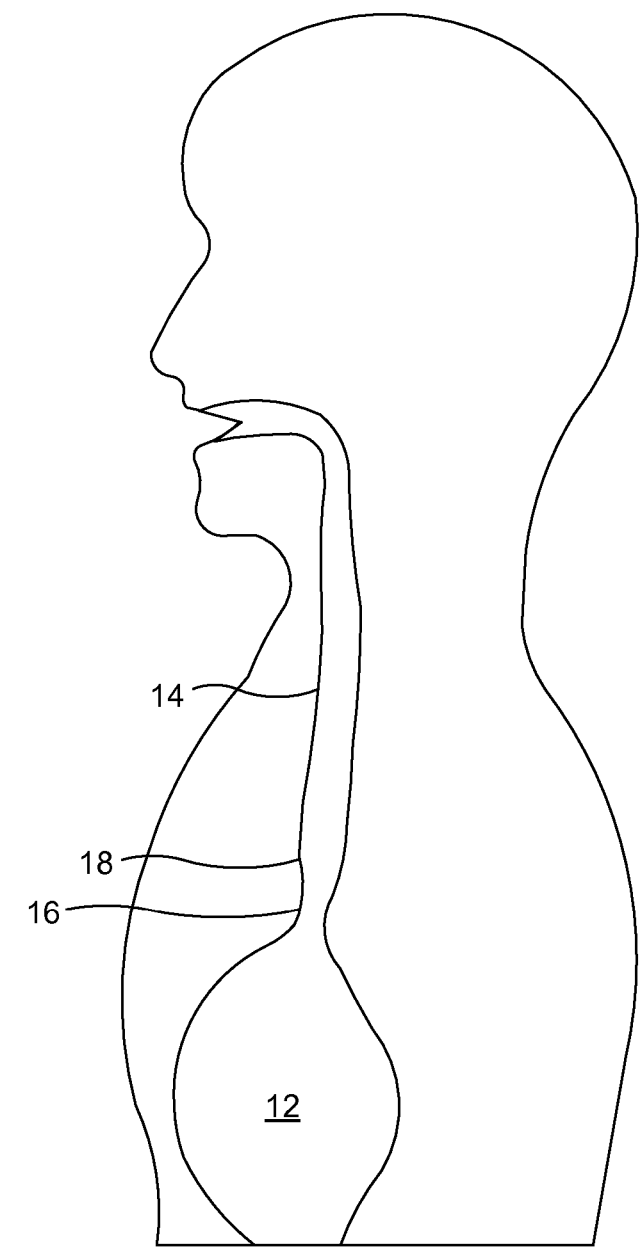
FIG. 1A is a schematic view showing an esophagus and stomach, to illustrate how one body lumen can be readily scanned using the present invention.

FIG. 1A includes a schematic illustration 10 showing a stomach 12, an esophagus 14, and a lower esophageal sphincter (LES) 16. LES 16 normally acts as a one-way valve, opening to enable food that is swallowed down the esophagus 14 to pass freely into stomach 12, but normally preventing acid and food from moving back up into the esophagus 14 from inside stomach 12. However, as noted above in the Background of the Invention, people suffering from chronic heartburn and gastroesophageal reflux often experience BE as a result of stomach acid passing through LES 16 and into the lower part of esophagus 14. Patients who are suffering from BE can be detected by determining whether the inner surface of the lumen comprising esophagus 14 has changed from its normal light pink color to a dark pink color in a region 18 that is just above LES 16. The exemplary scanning capsule enables region 18 within esophagus 14 to be readily scanned, producing images in which the presence of the darker pink color of the inner surface that is indicative of BE is clearly apparent. More importantly, as discussed in further detail below, it is contemplated that the scanning capsule may enable the scanning process to be carried out in an automated fashion, so that the detection of BE can be accomplished by a medical practitioner such as a technician or a nurse who is trained in the procedure, and normally, without any direct interaction by a medical doctor.

Figure 1B:
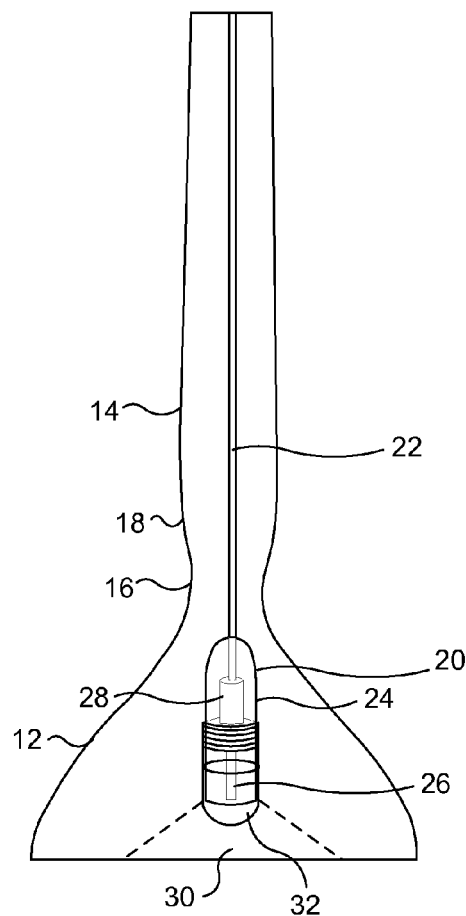
FIG. 1B is a schematic view of a portion of the esophagus and stomach of FIG. 1A, showing how the present invention is controllably disposed to scan a desired portion of the esophagus to detect a BE condition.

The manner in which an esophagus can be scanned is illustrated in FIG. 1B. As shown therein, a capsule 20 that is sized and configured for this purpose has been advanced through the interior of esophagus 14 and has just passed into stomach 12. Capsule 20 is coupled to a tether 22 that extends up through esophagus 14 and out through a patient's mouth. A housing 24 of the capsule is about the size of a large vitamin pill, e.g., about 15 mm long by 7 mm in diameter and comprises a plastic material that is biocompatible and not affected by stomach acid or other biological fluids. Tether 22 is extremely flexible and is relatively small in diameter, e.g., about 1 mm. Within housing 24, capsule 20 includes an actuator 28 that drivingly moves a scanner 26 to scan an inner surface of the lumen within a field of view (FOV) 30. When used to determine if a patient has BE, capsule 20 will typically be drawn back past LES 16 so that FOV 30 encompasses region 18. An image of region 18 that is provided by scanner 26 can thus be evaluated to indicate whether the tissue on the inner surface of esophagus 14 has turned the darker pink color indicative of BE. It will also be apparent that the inner surface of esophagus 14 can be scanned and imaged as capsule 20 initially descends toward stomach 12.

Figure 2:
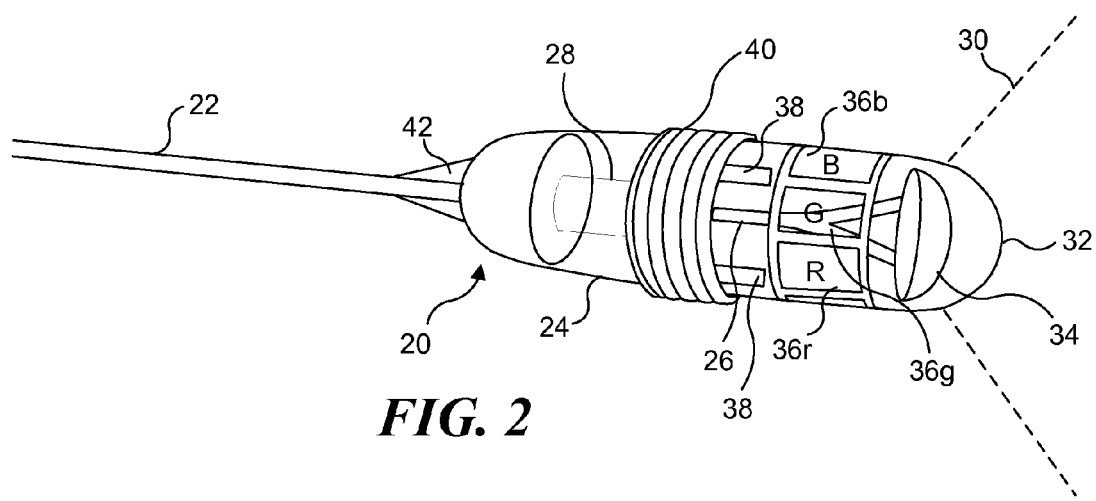
FIG. 2 is an enlarged isometric view of one embodiment of the present invention and indicating the relative wide field of view (FOV) provided by the scanner used therein.

FIG. 2 illustrates further details of this embodiment of capsule 20; a number of other exemplary embodiments of the capsule are discussed below. A forward or distal end 32 of housing 24 is optically transparent, so that light emitted by a vibrating optical fiber comprising scanner 26 in this exemplary embodiment, can pass through an optical system 34 that includes a plurality of lenses, reaching the inner surface of the esophagus or other lumen in which capsule 20 is disposed. While the inner surface may be illuminated by scanner 26 using other wavebands of light, in this exemplary embodiment, the inner surface of the lumen is illuminated using white light. Light reflected from the inner surface is detected by a plurality of red, green, and blue (RGB) sensors $36r$, $36g$, and $36b$, respectively. The white light that is used to illuminate the inner surface of the esophagus or lumen is conveyed to scanner 26 through an optical fiber (not separately shown) disposed within tether 22. The signals produced by the plurality of RGB sensors are conveyed back through electrical leads (not shown) within tether 22 for processing to produce an image corresponding to the portion of the inner surface that was scanned. In an alternative exemplary embodiment discussed below, the light reflected from the inner surface is conveyed proximally through optical fibers in the tether to detectors that are external of the patient's body.

The exemplary embodiment of FIG. 2 also includes position sensors 38, which respond to an external signal provided by a signal source (not shown) external to the body of the patient, by producing a signal indicative of a location, and optionally, an orientation of capsule 20 within the patient's body. A suitable position sensor, which responds to electromagnetic signals, is available, for example, from Ascension Technology. Position sensors 38 can respond to an electromagnetic field, an RF signal, a light signal of a wavelength selected to penetrate tissue and pass into the lumen, or another appropriate signal. Alternatively, it is also contemplated that position sensors 38 can be replaced by a signal source, which is used in connection with an external sensor (not shown) to determine the location, and optionally, the orientation of capsule 20 within a patient's body. The external signal source or position sensor can be disposed at a specific location on the body of a patient to provide a reference, by strapping the signal source or position sensor to a patient's torso at the specific location.

A chemical sensor 40 is optionally included to sense a chemical parameter. For example, chemical sensor 40 can detect hydrogen ion concentration, i.e., pH, within the lumen. Alternatively or additionally, the chemical sensor can include a temperature sensor for monitoring an internal temperature of the lumen. Similarly, a pressure sensor can be employed in addition to or in place of chemical sensor 40, which is thus intended to represent any one or all of these sensors.

As a further option, a selectively releasable connection 42 can be provided to pneumatically or electrically disconnect the capsule from the tether when desired. When thus released from its connection with the tether, the capsule will be conveyed through the body lumen and if the lumen is involved with the digestive tract, the capsule will pass through and be expelled. The releasable connection can be activated with a pressurized pulse that is propagated through a lumen (not shown) in tether 22 from an external source (not shown), or can be an electrical signal that magnetically actuates releasable connection 42 using an electrical current provided through a lead in the tether. A similar releasable joint might also or alternatively be provided near the proximal end of the tether, to release the tether and capsule to pass on through the lumen together.

System Processing Overview

Figure 3:
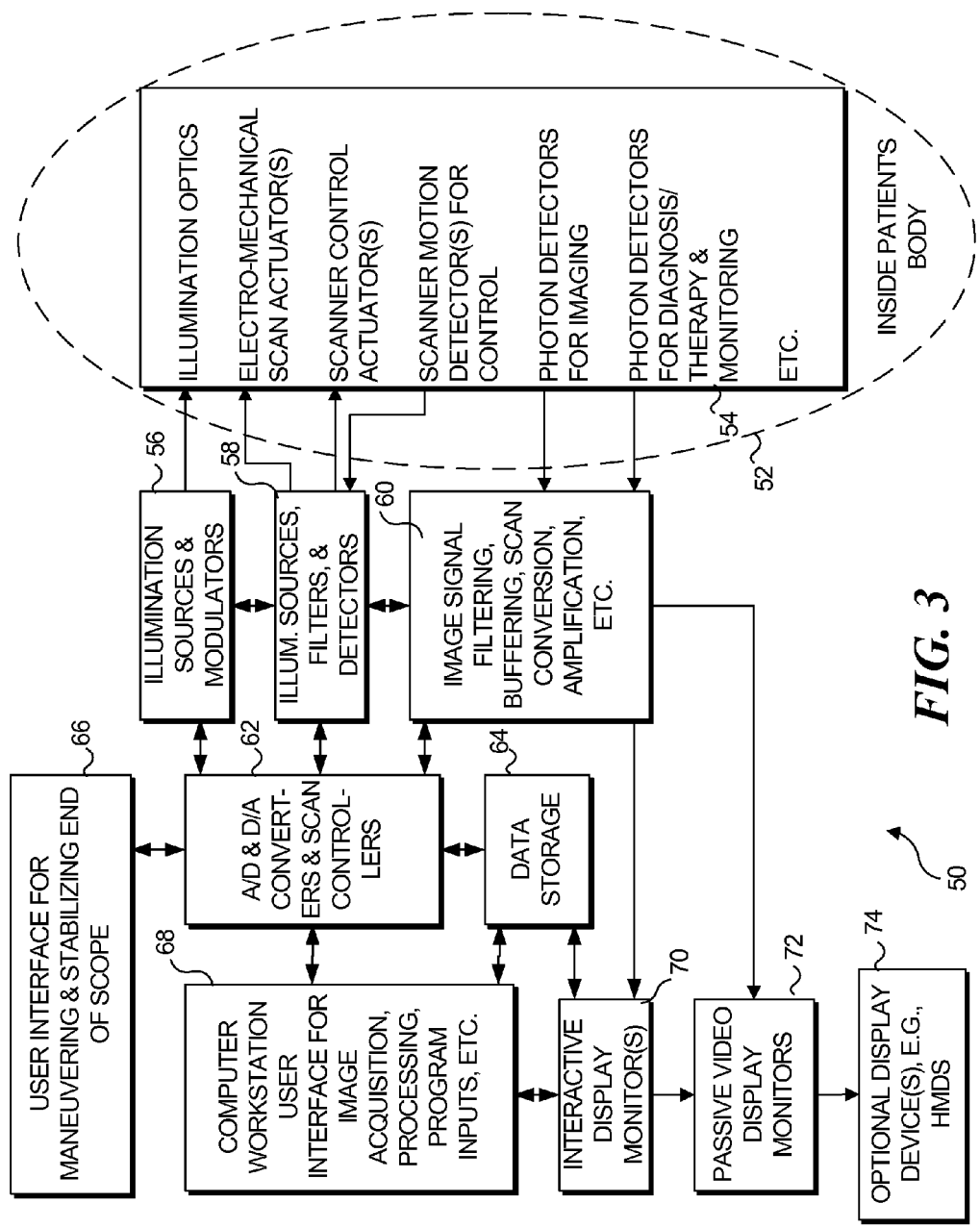
FIG. 3 is a block diagram illustrating the functional flow of signals in a scanning system in accord with the present invention, which is usable for monitoring, rendering diagnoses, and providing therapy to an inner surface of a lumen in a patient's body.

FIG. 3 illustrates a system 50, with external instrumentation, for processing the signals produced by various components that are inside the capsule and indicates how signals used for controlling the system are input to these components. In order to provide integrated imaging and other functionality, system 50 is thus divided into those components that remain external to the patient's body, and those which are in the capsule (i.e., the components within a dash line 52, some of which are optional depending upon the application in which this invention is being used). A block 54 thus lists the functional components that can be disposed within the capsule. As indicated in the Figure, these components include illumination optics, one or more electromechanical scan actuator(s), one or more scanner control actuator(s), one or more scanner motion detector(s) for control of the scanner motion, photon detectors for imaging a region of interest (ROI) (these photon detectors can alternatively be disposed externally if a light path is provided in the tether to convey the light reflected from the inner surface of the lumen to external detectors), and optionally, additional photon detectors for diagnostic purposes and for therapy and monitoring purposes (which can also be disposed externally of the capsule and patient). It should be noted that in regard to system 50, only the functional components actually required for a specific application, such as imaging an esophagus, may be included. Also, the additional functions besides imaging can be diagnostic, or therapeutic, or a combination of these functions, and can include taking a biopsy of tissue at an internal site for subsequent evaluation by carrying out an appropriate laboratory procedure. Although a specific embodiment of the capsule is not shown that includes a plurality of actuators, each associated with a different scanner, it will be apparent that due to the relatively small size of the scanners disclosed herein, it is possible to provide an array of such scanners to increase the total area scanned. Each such scanner will be provided with its own actuators and either with detectors to detect light from the region scanned by that scanner or with a waveguide to convey the light to one or more external detectors.

Externally, the illumination optics are supplied light from illumination sources and modulators, as shown in a block 56. Further details concerning several preferred embodiments of external light source systems for producing RGB, UV, IR, and/or high intensity light conveyed to the distal end of an optical fiber system are disclosed below. A block 58 indicates that illumination sources, modulators, filters, and detectors are optionally coupled to the electromechanical scan actuator(s) within the capsule, and/or to the scanner control actuators provided in the capsule. Scanner motion detectors are optionally used for controlling the scanning and produce a signal that is fed back to the scanner actuators, illumination source, and modulators to implement more accurate scanning control, if needed.

In a block 60, image signal filtering, buffering, scan conversion, amplification, and other processing functions are implemented using the electronic signals produced by the imaging photon detectors and for the other photon detectors employed for diagnosis/therapy, and monitoring purposes. Blocks 56, 58, and 60 are interconnected bi-directionally to convey signals that facilitate the functions performed by each respective block. Similarly, each of these blocks is bi-directionally coupled in communication with a block 62 in which analog-to-digital (A/D) and digital-to-analog (D/A) converters are provided for processing signals that are supplied to a computer workstation user interface employed for image acquisition and processing, for executing related programs, and for other functions. The computer workstation can be employed for mass screening of the population when programmed to process images produced by scanning inside an esophagus to detect BE so that near real-time results are provided, and normally without requiring a physician's evaluation.

Control signals from the computer workstation are fed back to block 62 and converted into analog signals, where appropriate, for controlling or actuating each of the functions provided in blocks 56, 58, and 60. The A/D converters and D/A converters within block 62 are also coupled bi-directionally to a block 64 in which data storage is provided, and to a block 66. Block 66 represents a user interface for maneuvering, positioning, and stabilizing the capsule with the scanner inside a lumen within a patient's body. Further description of several exemplary techniques for determining a location of a capsule in a lumen are discussed below. The procedure for maneuvering and positioning the capsule in a lumen is discuss in further detail below. Also discussed is a technique for stabilizing the capsule in the lumen.

In block 64, the data storage is used for storing the image data produced by the detectors within a patient's body, and for storing other data related to the imaging and functions implemented by the scanner in the capsule. Block 64 is also coupled bi-directionally to the computer workstation and to interactive display monitor(s) in a block 70. Block 70 receives an input from block 60, enabling images of the ROI on the inner surface of the lumen to be displayed interactively. In addition, one or more passive video display monitors may be included within the system, as indicated in a block 72. Other types of display devices, for example, a head-mounted display (HMD) system, can also be provided, enabling medical personnel to view an ROI in a lumen as a pseudo-stereo image.

Figure 4:
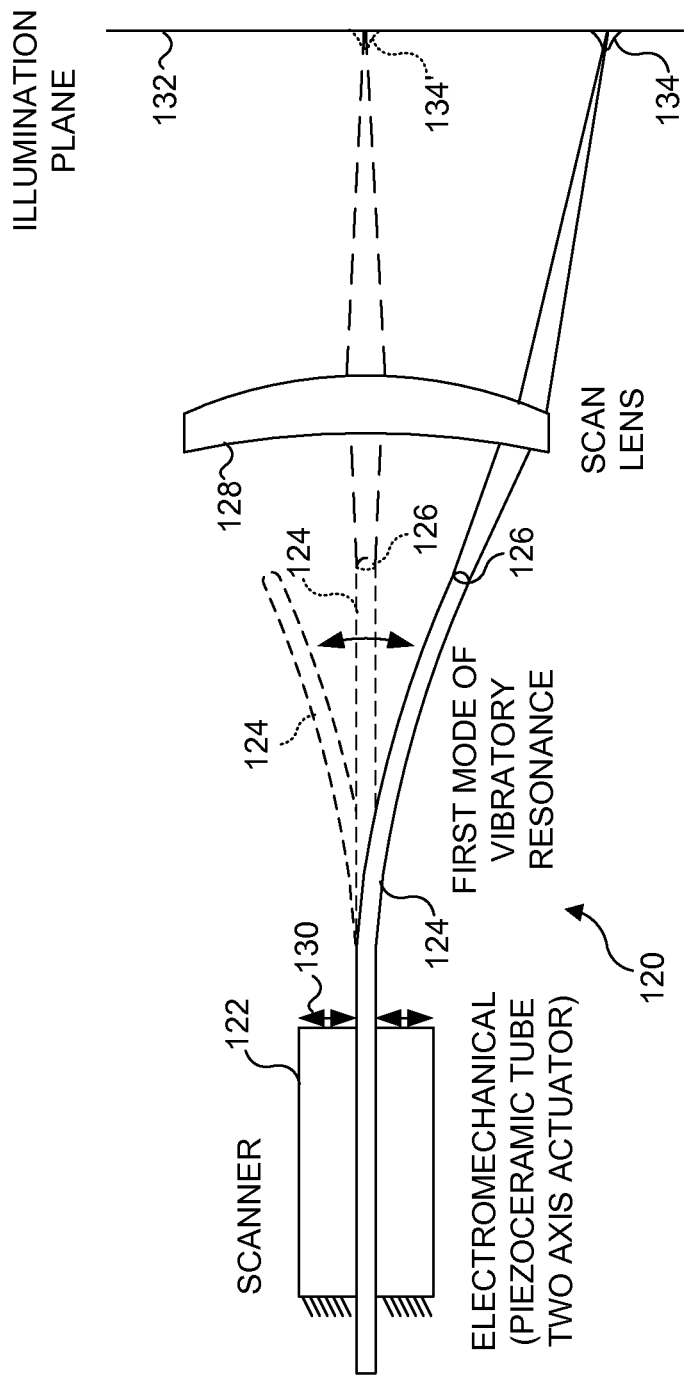
FIG. 4 illustrates a scanner embodiment having an actuator for driving a scanning optical fiber with a microlens, for use as an optical beam scanner with a scan lens, in connection with the present invention.

FIG. 4 illustrates one exemplary embodiment of a scanner 120 that can be used in the capsule. Scanner 120 includes an electromechanical device or piezo-ceramic tube actuator 122 that causes a first mode of vibratory resonance in a cantilevered optical fiber 124. In this exemplary embodiment, the cantilevered optical fiber includes a collimating lens 126 at its distal end and a scan lens 128 that directly focuses the optical beam of light that has passed through the collimating lens onto an illumination plane 132, which typically would comprise a region on the inner surface of a lumen. Light focused by scan lens 128 forms a point spread function (PSF) 134 on illumination plane 132 and as the cantilevered optical fiber moves, a PSF 134' moves over the illumination plane. Although cantilevered optical fiber 124 can be limited to scanning along a single axis as indicated by arrows 130, it is typically preferable to use an actuator that moves the optical fiber so that it scans two-dimensionally, e.g., in a spiral pattern. However, at a high amplitude resonance vibration produced by a linear single axis actuator, the resulting motion of the optical fiber can be in two dimensions due to nonlinear cross-coupling of mechanical forces. Thus, two axis actuators are not required for two-dimensional (2-D) scanning.

Figure 5:
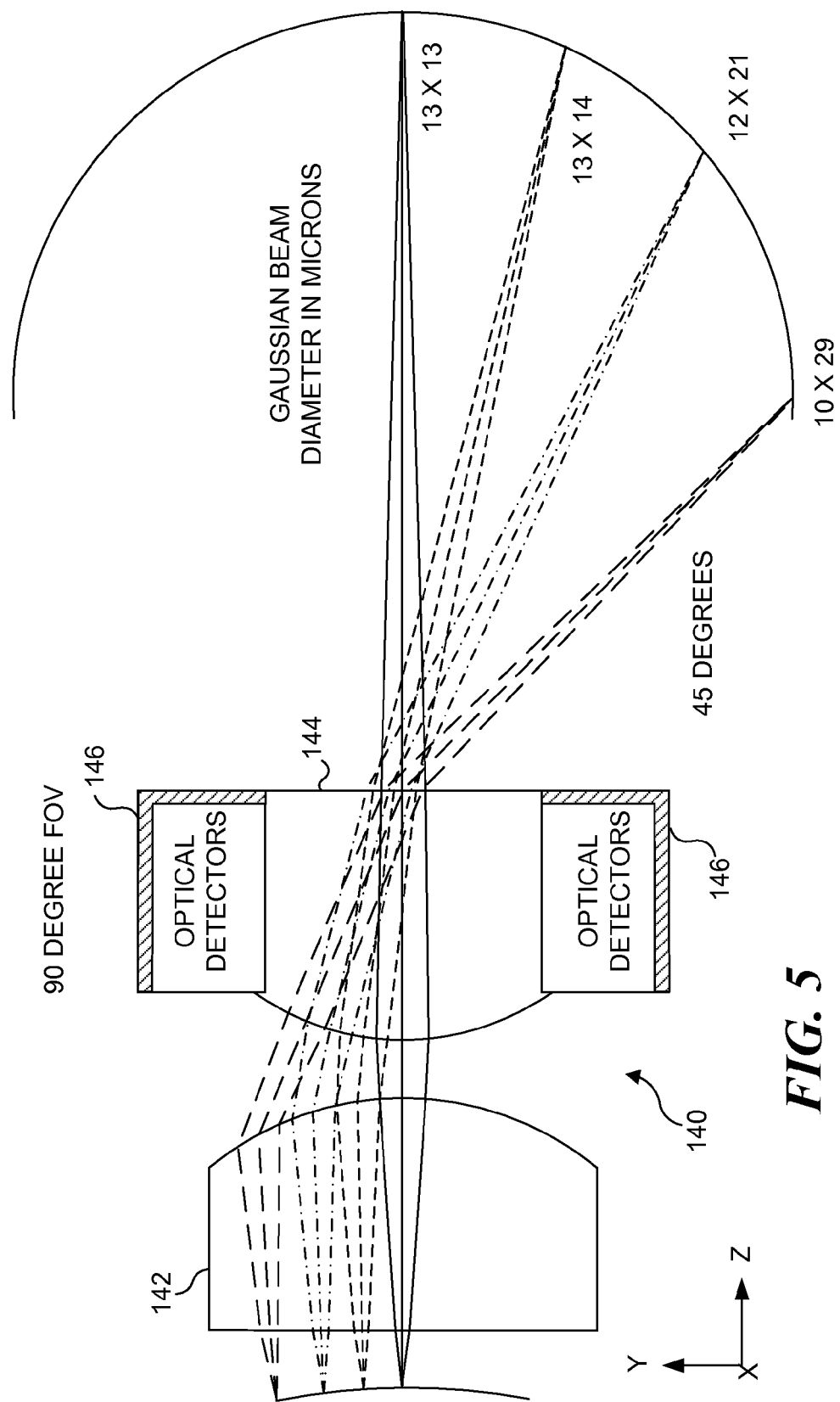
FIG. 5 is a schematic view of a point-source imaging embodiment, illustrating the variations in the imaged spot diameter at different scanning angles, in connection with a scanner used in the present invention.

FIG. 5 graphically illustrates an advantage of the scanners used in the present invention. Such fiberoptic scanners are readily capable of achieving a 120° FOV by imaging the scanned point-source object plane to a magnified image plane, which typically would comprise a region on the inner surface of a lumen. In contrast to FIG. 4, which illustrates optical beam scanning, FIG. 5 depicts an exemplary embodiment of point source imaging that uses imaging lenses rather than the combination of a microlens and a scan lens. FIG. 5 also illustrates the relative Gaussian beam diameters of the light used for illumination, at different angles between zero and 45°, for one exemplary embodiment of an optical system 140 that includes lenses 142 and 144. In this embodiment, detection of reflected light is carried out using optical detector 146 that is disposed on and around the outer periphery of lens 144 (this portion of the lens does not transmit the illumination light), or alternatively, light reflected from the region being scanned can be collected and conveyed through optical fibers to external detectors (not shown). While shown in cross-section, it will be understood that optical detector 146 wraps around the entire periphery of lens 144 and actively detects light both on its forward surface and on all sides, as indicated by the hatched light sensing portions thereof.

Figure 6A:
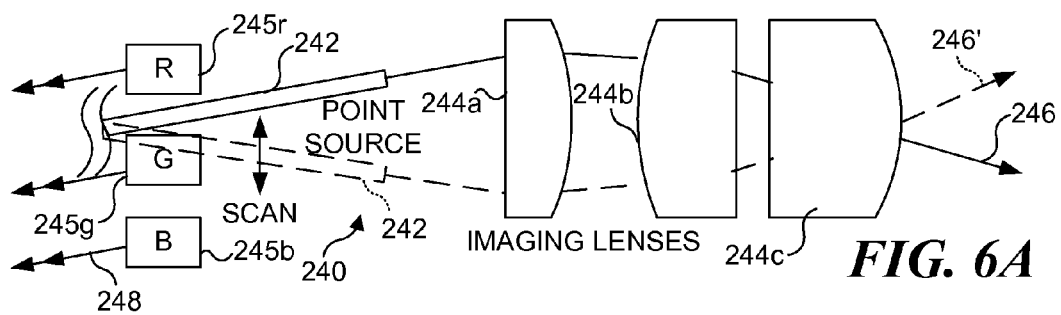
FIG. 6A is a schematic view of a scanning point-source illuminator with time-series photon detectors and imaging lenses for use in a scanner of the present invention.
Figure 6B:
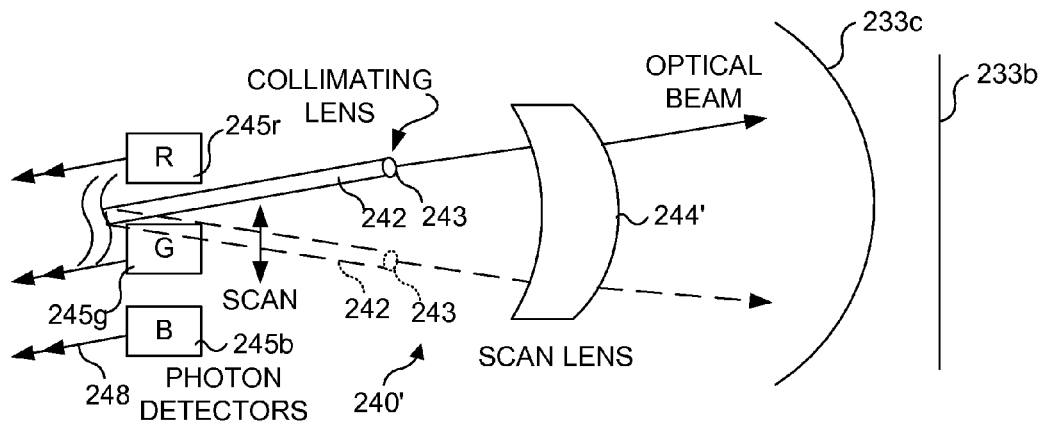
FIG. 6B is a schematic view of a scanning optical beam illuminator with a scan lens and detectors, for use in a scanner of the present invention.

FIGS. 6A and 6B illustrate embodiments of 2D scanning point-source illuminator 240 and optical beam illuminator 240' for use in the capsule. In FIG. 6A, point-source illuminator 240 has the capability of providing a point source illumination through an optical fiber 242 within a capsule that is caused to scan an ROI on the inner surface of a lumen within a patient's body. Light emitted by the scanning optical fiber is transmitted through imaging lenses 244a, 244b, and 244c to illuminate different portions of the ROI as the point source provided by the scanning optical fiber is caused to move in a desired pattern within the capsule (not shown). In the position illustrated with solid lines, a light beam 246 illuminates a particular portion of the ROI, while in the position illustrated by dash lines, the scanning optical fiber produces light beam 246' that illuminates a different portion of the ROI. Light reflected from each successive point illuminated by the scanning optical fiber is reflected back through imaging lenses 244c, 244b, and 244a and is received by RGB photon detectors 245r, 245g, and 245b, respectively, which produce corresponding electrical signals that are transmitted outside the patient's body for use in displaying a full color image of the ROI. Alternatively, the light can be conveyed through the tether to external photon detectors disposed outside the patient's body.

In addition, therapy can be rendered to the inner surface of a lumen using scanning optical fiber 242. For example, by illuminating the points scanned by it using a relatively high powered laser, high intensity light for the purposes of drug activation or photodynamic therapy (PDT), or thermotherapy can be applied to the ROI. Since the signals produced by the RGB photon detectors correspond to successive points in the ROI, the image resulting from the signal that they produce is based upon a time series accumulation of image pixel data. Scanning optical fiber 242 is preferably a single mode or hollow optical fiber, of telecommunications grade or better. One significant advantage of this integrated system is that the mechanisms employed for generating the visual image are the same used for diagnostic, therapeutic, and surgical procedures. The directed optical illumination employed for image acquisition enables the most sophisticated diagnoses and therapies to be integrated into this single imaging system within a capsule sized to pass through a body lumen (by sharing the scan engine, display, and user interface).

FIG. 6B illustrates a scanning optical beam illuminator 240' for use in a capsule (not shown) and which also includes scanning optical fiber 242, just as the exemplary embodiment shown in FIG. 6A. However, instead of using imaging lenses, scanning optical beam illuminator 240' employs a collimating lens 243 that is attached to the distal end of the scanning optical fiber and a scan lens 244'. The light conveyed through optical fiber 242 as it moves within the capsule is collimated by collimating lens 243 and then focused onto a flat illumination plane 233b, or a curved illumination plane 233c, corresponding to the ROI on the inner surface of a lumen within a patient's body. Light reflected from each successive point that is scanned as the scanning optical fiber moves passes back through scan lens 244' and is detected by RGB photon detectors 245r, 245g, and 245b, which respectively provide the RGB signals over lines 248 that are used to produce an image, with data accumulated pixel-by-pixel.

At the illumination plane, the beam of optical radiation is focused to achieve maximum intensity and/or optical quality, which is the goal for all modes of scanning. When tissue is coincident with the illumination plane, the optical irradiance is a function of the optical power and size of the light spot on the tissue. Thus, with regard to imaging, diagnoses, and therapy, the resolution of the scanner disposed in the capsule is determined by this spot size at the image plane and may also be limited by the sampling density (i.e., samples per unit area of tissue), since higher resolution is achieved by providing more scan lines per area. With regard to image acquisition, the image resolution is determined by the illumination spot size, detector bandwidth (and scan rate), and signal-to-noise ratio (illumination intensity and collection efficiency), while image resolution is not limited by the physical size or number of the photon detectors.

Since diagnoses and therapies require accurate spatial discrimination, there is a need for directed illumination that is pre-calibrated before delivery. By integrating the optical imaging with diagnostic and therapeutic scanning delivered in a capsule, a medical practitioner can easily see the spatial discrimination of the optical scanning by viewing the displayed image before proceeding to diagnostic or therapeutic applications within the lumen in which the capsule is disposed. Finally, the integration of computer image capture electronics and image processing software enables the image, diagnostic, and therapeutic data to be analyzed on a pixel-by-pixel basis. Since each pixel corresponds to the same area or volume of tissue, the single fiber integrated system maintains spatial registration for all three functions; imaging, diagnosis, and therapy. Consistent spatial registration from the same point of view for all three functions makes the single optical fiber scanning system, delivered within a capsule passing through a lumen, highly accurate and easy to use by medical practitioners.

The advantages afforded by using the scanning device integrated within a relatively small capsule are:
  Smaller size with integration;
  Little or no sedation of the patient;
  Physician is not required to insert the tethered capsule into a patient's esophagus;
  Lower cost with integration and use of low cost components;
  Lower flexural rigidity to allow greater access within various lumens in the body;
  Faster procedural times, especially if requiring reiterations of therapy;

Greater accuracy with integrated high-resolution imager and interactive display;

Additional features with scanning optical system, such as variable resolution (real-time zooming) and enhanced stereo effects (such as shading);

Additional functionality with integrated non-visible optical sources and detectors;

Lower risk to patient for infection from multiple tools or multiple insertions within a lumen;

Faster recovery times for patient with less healthy tissue damage; and

Able to be left inside the body for extended periods of time to monitor chronic diseases.

Figure 6C:
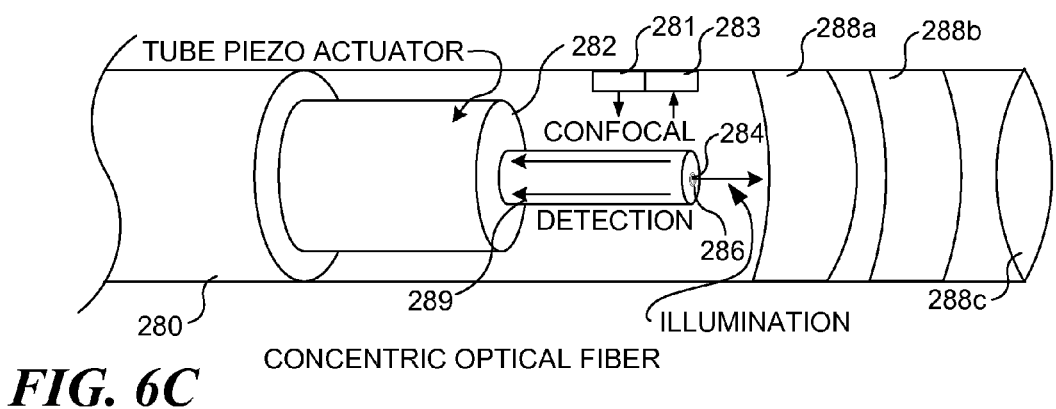
FIG. 6C is a schematic diagram showing a configuration for a scanner using a bundle of optical fibers and a single concentric core optical fiber.

FIG. 6C illustrates a portion of a concentric optical fiber assembly 280 for use as a confocal scanner that is readily employed with the capsule of the present invention. Optical fiber assembly 280 includes a relatively small central optical fiber 284, which is surrounded by cladding 286. A larger diameter optical fiber surrounds the smaller optical fiber. Illumination of an ROI is provided through small diameter optical fiber 284, and light emitted thereby passes through lenses 288a, 288b, and 288c to illuminate the ROI. Light reflected or otherwise received from the ROI is focused by these lenses back into an optical fiber assembly 289, which conveys the light that is received, through the tether, to detectors and other instrumentation disposed outside the patient's body. It should be noted that a single optical fiber can both illuminate the ROI and convey light from the ROI to the external instrumentation in this so-called concentric confocal imaging. The concentric optical fiber geometry is a single mechanical unit either fused together upon heating pulling from a preform, or alternatively, the concentric regions of refractive index differences can be manufactured by doping the glass fiber radially. A tubular piezoelectric actuator 282 causes the concentric optical fibers to move together and thus to scan the ROI in one of the modes described above. The light collected in the surrounding optical fiber can be used with signals from detectors or optical fibers at radially increasing distances from the reflected confocal point to enhance image analysis and refine the depth of light penetration for diagnosis, imaging, and therapy. In extremely high-gain or discrimination detection configurations, the backscattered light may be collected in the same part of the waveguide (e.g., the core of the optical fiber). Such applications will use the optical coherence property to amplify the small signal level, producing diagnostic maps based upon optical coherence reflectometry (OCR) or optical coherence tomography (OCT), or laser-induced feedback.

FIGS. 6D and 6E illustrate an embodiment of a scanner useful within the capsule of the present invention, which includes detectors for RGB, ultraviolet (UV), and infrared (IR) spectral components. An optical fiber assembly 295 includes an internal actuator 291 mounted on a support 293 within the capsule (not shown). An optical fiber 300 enclosed within the housing having an opening 298 extends distally of actuator 291 and is moved by the internal actuator, which is preferably a tubular piezoelectric type, so as to achieve a desired scanning pattern, such as a helical or spiral scan. RGB detectors 292 and 294 are disposed above and below optical fiber 300, while RGB detectors 306 and 308 are disposed to the left and right of the optical fiber, as illustrated in FIG. 6E. In addition, RGB detectors 290 and 296 are disposed on the outer surface of the assembly on the top and bottom thereof, as indicated in these Figures. In a similar manner, RGB detectors 302 and 304 are mounted on the left and right sides of the detector as illustrated in FIG. 6E. UV detectors 310 and 312 are mounted on one of the diagonals between the RGB detectors, while IR detectors 314 and 316 are mounted on the other diagonal. Accordingly, a pseudo-stereo image can be produced in regard to the RGB, UV, or IR spectral components received by the various detectors included on this assembly, when imaging tissue on the inner surface of a lumen, from within the capsule of the present invention. By comparing signals from the multiple RGB detectors and knowing the orientation of the tethered capsule within the lumen, the level of the signal due to specular reflection and multiple scattering can be estimated and reduced by appropriate signal processing.

FIGS. 6F and 6G illustrate an optical fiber assembly 295' in which parallel and perpendicular polarized light detectors are included. Optical fiber 300 conveys light that is polarized in a parallel direction as indicated by reference numeral 328. On opposite sides of optical fiber 300 are disposed parallel polarized light detectors 334 and 336, while above and below optical fiber 300 are disposed perpendicular polarized light detectors 324 and 326, as shown in FIG. 6G. In addition, perpendicular polarized light detectors 320 and 322 are disposed above and below perpendicular polarized detectors 324 and 326, while parallel polarized light detectors 329 and 330 are disposed left and right of parallel polarized light detectors 334 and 336. Optical fiber assembly 295' is thus usable within a capsule to detect polarized light in both orientations, where the light is reflected or otherwise received from an ROI on the inner surface of a lumen, for analysis by instrumentation disposed external to the patient's body that receives the detector output signals through the tether that is coupled to the capsule (neither shown in these Figures). The signal produced by the various polarized light detectors can also be used for producing an image of the tissue inside the lumen, corresponding to that specific type of polarization, for display externally. By recording light that is shifted in polarization due to interaction with the tissue, specular reflection can be minimized. Since the degree of polarization from the tissue partially depends on tissue optical properties, various tissue types and depths can be discriminated by measuring both axes of polarization.

FIG. 7A illustrates an exemplary scanning and detection system 266 that can be used with a capsule for providing both a pseudo-stereo image of an ROI on the inner surface of a lumen and for acquiring a spectral image that can be analyzed with a spectrophotometer externally of the lumen. In this system, an optical fiber assembly 250, which comprises the tether extending through the lumen and outside the patient's body includes an optical fiber 256 that is tapered at its distal end and is surrounded by a piezoelectric actuator 254. Actuator 254 causes optical fiber 256 to vibrate and scan an ROI, emitting light that passes through lenses 258a and 258b to illuminate the inner surface of the lumen (not shown). Light reflected from the ROI from this tissue or light otherwise received therefrom (such as phosphorescent or fluorescent emissions) is collected by twelve optical fibers 252 that are arranged in a circumferential array around optical fiber 256. As illustrated in this exemplary embodiment, optical fibers 1, 2, and 3, which are collectively referred to by a reference number 260, are respectively coupled through the tether to external RGB imaging detectors corresponding to a left side of the circumferential array. Similarly, optical fibers 7, 8, and 9, which are collectively identified by a reference number 262, are respectively coupled through the tether to external RGB imaging detectors for the right side of the circumferential array. Another set of optical fibers 264 are coupled through the tether and connected to a spectrophotometer 270. The spectrophotometer is employed for spectral analyses and spectral image acquisition using UV, visible, and/or IR light.

Since the RGB detectors for the left and right side of the circumferential array receive light from the ROI at two spaced-apart portions of the array (i.e., the left and right sides), they produce a pseudo-stereo full color image that is readily viewed using an HMD display (not shown).

A schematic diagram illustrating an exemplary light source system 340 for producing light of different spectral composition that is coupled through the tether and into an optical fiber 360 disposed within the capsule is illustrated in FIG. 7B. In this embodiment, a red light source 342, a green light source 344, a blue light source 346, and an UV light source 348 are each selectively coupled into optical fiber 360. Optical fiber 360 extends through the tether so that the distal end of the optical fiber emits light to illuminate tissue on the inner surface of a lumen through which a capsule that includes the distal end of the optical fiber is passing. Attenuators 350 are provided at the proximal end of the optical fiber for each of the light sources so that the intensity of the light they produce can be selectively controlled. Three dichroic mirrors 352, 354, and 356 that include coatings specific to the color of light emitted by each of the corresponding green, blue, and UV light sources are positioned within the light path to reflect green, blue, and UV light, respectively, into the proximal end of optical fiber 360. Light that is outside the reflectance waveband for each of these dichroic mirrors is passed through the dichroic mirror and is focused by a lens 358 into the proximal end of optical fiber 360.

An alternative light source system 362 for use with the present invention is illustrated in FIG. 7C. In this embodiment, red, green, and blue light sources 342, 344, and 346, respectively, are coupled through optional attenuators 350 to a series or sequence of optical couplers 366 through lenses 364. Lenses 364 focus the light from each of the different colored light sources into optical fibers 365, which convey the light to optical couplers 366. In addition, an IR source 368 transmits light through an optional attenuator 350 and a lens 364 into optical fiber 365, which conveys the IR light to the last optical coupler in the sequence. Optical detectors 369 are provided for monitoring the light intensity levels or power levels for each of the different sources of light, enabling the intensity of the various light sources to be controlled. From the last optical coupler, an optical fiber 367 conveys light to an input to optical detectors 369, while the output from the last optical coupler is input to the proximal end of optical fiber 360 for input through to the scanner disposed within a capsule in a lumen inside a patient's body (neither the tether comprising optical fiber 360 or the capsule are shown—to simplify this drawing).

As indicated above, it is desirable to develop a scanning device with a small cross-sectional area that can be manufactured at relatively low cost and high volume to ensure that the endoscopic capsule scanning system is economical and thereby facilitate its widespread use. Micro-electromechanical systems (MEMS) technology using an integrated thin film device may be beneficially employed when producing economical scanners to more readily achieve this goal. FIGS. 8A, 8B, and 8C illustrate an exemplary thin film optical system 370 that can be adapted for use as a scanner within a capsule for use in scanning applications. A further exemplary alternative 370' illustrated in FIG. 8D includes parallel cantilevered thin film optical waveguides for scanning and detectors.

In this thin film exemplary embodiment of a scanner, electrostatic actuators 386 act on a thin film optical waveguide 380, which is supported on a raised ledge 378. The thin film optical waveguide is only about 0.003 mm in diameter. A distal portion 382 of the thin film optical waveguide is caused to scan in the two orthogonal directions indicated by the curved arrows in FIGS. 8A and 8B. It should be noted that the scanning motion can be one-dimensional (i.e., along a single axis), or as shown, in two dimensions (e.g., following either a raster pattern or a spiral pattern). Optionally, the thin film optical device can be mounted in the capsule on a rod 373, which is then manually or mechanically rotated or vibrated to change the orientation or displace the single axis scan. Also provided is a lens 384 that can be mounted to a silicon substrate 376 (or other substrate material). As an alternative, actuators (not shown), which are external to the substrate but still disposed in the capsule, can be used instead of the electrostatic actuators, in which case, an optical fiber 374 and lens 384 would be supported by silicon substrate 376. The optical fiber would be caused to vibrate by the external actuators, causing the cantilevered thin film optical waveguide to resonantly scan as desired pattern.

Optical fiber 374 can be affixed to silicon substrate 376 within a centering V notch 390 to ensure that it is aligned with thin film optical waveguide 380. Since the optical fiber is approximately 0.1 mm in diameter, care must be taken to provide accurate alignment between the ends of the optical fiber and the thin film optical waveguide. FIGS. 8A and 8B show an exemplary embodiment using butt-end coupling between optical fiber 374 and a thin film optical waveguide 380. To ensure appropriate alignment between the optical fiber and the thin film optical waveguide, V notch 390 precisely establishes a disposition of the optical fiber relative to the thin film optical waveguide. An index-matching gel 375 or fluid can be used to couple light from optical fiber 374 to thin film optical waveguide 380. To reduce the gap filled by index-matching gel 375, the tip of the optical fiber can be etched to form a taper. Further, the tip length and surface can be adjusted by $CO_2$ laser machining before affixation. Other embodiments of the MEMS scanner described below further alleviate alignment problems.

In the embodiments shown in FIGS. 8A, 8B, and 8C, light reflected back from a target in the ROI passes through lens 384 and is received by RGB detectors 392r, 392g, and 3926b, respectively. These detectors, disposed in the capsule, respond to the light of the corresponding color, producing a signal that is conveyed proximally to the external components, as discussed above. In FIG. 8D, separate image and diagnostic/therapeutic thin film optical waveguides are spaced apart and scanned in parallel; this exemplary embodiment uses a diagnostic "DIAG" detector 392d.

Automated System for Mass Screening

One of the contemplated uses of the present invention is that it might eventually enable a nearly automated esophageal screening process to be carried out by a medical practitioner (not requiring that the procedure be done by a medical doctor) to screen a patient for BE. FIG. 9 illustrates an automated system for use in connection with the present invention for conducting scanning of the inner surface of the esophagus of a patient 395 by a medical practitioner 408, to determine if the patient is afflicted with BE (or some other condition of the esophagus). This system includes a computer processor 394, which carries out many of the functions discussed above in connection with FIG. 3 and in further detail below.

Tether 22 is coupled to computer processor 394 after passing through a non-contact axial motion measuring device 396 that is used for monitoring the movement of tether 22. As explained above, tether 22 is used for retracting or enabling advancement of a capsule within the esophagus of patient 395. An electrical cable 402 conveys a signal produced by non-contact axial motion measuring device 396 that is indicative of the position or axial movement of the tether, to computer processor 394. Tether 22, which includes one or more optical fibers and one or more electrical leads that convey optical and electrical signals to and from the scanner disposed in the capsule (neither shown in this view), is retracted or allowed to advance in the esophagus with the capsule. The tether extends between lips 404 and down the esophagus of the patient. Indicia (e.g., magnetic or optical as described in detail below, enable the position and movement of the tether to be detected as the tether passes through device 396. Patient 395 is initially provided a glass 406 of liquid, such as water, to facilitate swallowing the capsule and attached tether 22. The liquid is swallowed after the capsule is inserted into the patient's mouth and helps to advance the capsule through the esophagus with the normal peristalsis of the muscles comprising the walls of the esophagus as the patient swallows the liquid.

The capsule is allowed to advance into the stomach of the patient and is then withdrawn past the LES by medical practitioner 408 grasping handle 402 and rotating reel 396. Additionally, it is possible that a computer-controlled withdrawal of the capsule might use a motorized reel (not shown) to fully automate the screening process by withdrawing the capsule up through the esophagus. Thus, the computer might determine how fast to withdraw the capsule, in response to criteria that determine the quality and content of the images being scanned by the capsule in real time, and in response to the signal output from non-contact axial motion measuring device 396. In addition to controlling the speed of the withdrawal of the capsule, the computer can control the intensity of light provided for scanning and patient-specific variables, and can carry out automated image stitching to form panoramic images of the interior surface along a length of a lumen. An example of currently available automated image stitching software is available, for example, from Matthew Brown as "AutoStitch," (see the URL regarding this software at http://www.cs.ubc.ca/~mbrown/autostitch/autostitch.html). Such images can be used in connection with image recognition software to determine the location of the LES and to automate the determination of whether a patient has BE or some other medical problem. Also, images automatically stitched together to form a full 360° panoramic view can be calibrated to form a ruler-like measure in pixels of the length of the capsule from the LES, as an alternative measure to define the location of the capsule in a patient's esophagus. As a further alternative, the signal produced by non-contact axial motion measuring device 396 may be employed to speed up the process of stitching together the successive axial images of a lumen such as the esophagus, to form the full continuous panoramic image of the lumen.

By viewing a display 398 that is coupled to computer processor 394, the medical practitioner can readily observe images of the stomach and then, as the reel rewinds the tether to retract the capsule above the LES, the medical practitioner can observe images of the inner surface of the esophagus on the display. An indicator 400b is displayed at one side of the display to show the relative speed and direction with which the capsule is moving through the esophagus.

Computer processor 394 can detect the LES based upon the changes in an image 399 and display a distance 400a of the capsule above the LES, and can be programmed to automatically evaluate the images of the portion of the inner surface of the esophagus immediately above the LES to determine if the patient has the characteristic dark pink color at that point, which is indicative of BE. The medical practitioner should only be required to manipulate tether 22 and assist the patient in initially swallowing the capsule, since the results of the image scanning process can thus be sufficiently automated to detect the condition of the esophagus in near real time, providing an immediate indication of whether the patient is afflicted with BE. The efficiency of such a system should thus enable mass screenings of the population to be conducted at minimal cost, so that esophageal cancer of which BE is often a precursor, can be avoided by early detection of BE.

Functional Block Diagrams

FIG. 10 illustrates at least some of the variety of functions that can be carried out with the exemplary scanning system when the capsule is disposed within a lumen of a patient's body. Functions such as diagnosis, therapy, and monitoring are shown in blocks that are formed with dash lines, while solid lines are used for imaging functions of a system 410 that is implemented with the capsule and related components. As illustrated in this Figure, imaging lasers 412 produce light that is directed into a patient's body via the tether and directed by the scanner in the capsule, through imaging optics used with the scanning optical fiber that is disposed in the capsule. Furthermore, diagnostic, therapeutic, and monitoring lasers in a block 416 that can be controlled by a remote optical switch and attenuators in a block 418 produce coherent light conveyed through an optical coupling mechanism 420 to additional optical components 422 disposed inside the capsule for use within the lumen of a patient's body. RGB photon detectors 430 respond to light received from the ROI on the inner surface of the lumen, producing an electrical signal that is conveyed through electrical conductors within the tether or running along side it, to instrumentation disposed outside the patient's body. Alternatively, the RGB light can be conveyed through optical fibers within the tether to external photon detectors 426 outside the body, or to other types of optical detectors 424 that include, for example, photodiodes and related circuitry.

As indicated in a box 432, the exemplary system may include additional high or low power UV, and/or visible, and/or IR detectors associated with collection optical fibers for use by one or more spectrophotometers or spectrum analyzers. For example, spectrophotometers and spectrum analyzers indicated in a block 434 can receive light conveyed through light collection optical fibers and/or as signals conveyed over conductors as indicated in a block 436. The system may include additional photon detectors disposed inside the capsule within the patient's body as a further option. Signals are exchanged bi-directionally between block 432 and 434 and a computer processor (or workstation) and data acquisition component in a block 440. The computer processor can execute algorithms that provide for non-linear scanning patterns and control algorithms and also can be programmed to carry out intensity data acquisition, image mapping, panoramic image stitching, and storage of data. In addition, tasks including real-time filtering (e.g., correction for motion and scanner artifacts), real-time determination of ratios and background subtraction, deconvolution, pseudo-stereo enhancement, and processing of the signals produced by the various detectors are implemented by the computer processor. Signals provided by the computer processor are output to image display devices (such as shown in FIG. 9) and for data storage on non-volatile storage (not shown). The image display devices may include cathode ray tube, liquid crystal displays, and HMD devices or other types of stereographic displays, as noted in a block 442.

Since commercially available displays typically require rectilinear video format, any non-rectilinear optical scanning patterns must be stored in data buffers (memory) and converted to the standard raster scanning format for the display monitors, to make use of the many advantages of non-rectilinear scanning, (such as a simplified single actuator, cylindrical scanner size, and lower scanning rates) used for the one or more scanners in the exemplary capsule. This additional step in signal conditioning and remapping is technically trivial with programmable computing devices.

In addition, image analysis software for carrying out spectral and multivariate analysis and for locating and calculating the limits of regions of interest are carried out using the computer processor or other computing device. In regard to the ROI on the inner surface of the lumen, the computations may determine its distribution, boundary, volume, color, and optical density, and based upon the data collected from the ROI, can determine a tissue disease state such as BE, and medical staging, as well as calculate and monitor therapeutic dosage. All of these functions are indicated in a block 444, which may use the normal imaging computer processor of block 440. Block 444 is coupled to a block 446, in which additional interactive displays and image overlay formats are provided. Associated with block 444 is a block 448, which indicates that scanner power and control electronics are provided for actuating the electromechanical scanner and for receiving signals from servo sensors in a block 450, which are used for both normal image acquisition and enhancements involved in screening, monitoring, and diagnosis, as well as pixel accurate delivery of therapy to a desired site within the lumen.

Various embodiments of optical fiber scanning actuators have been described above, in connection with moving a scanner disposed in the capsule to image an ROI within a lumen. A block 454 indicates that provision is made for manual control of the distal tip of the scanning optical fiber, to enable the capsule containing the scanning optical fiber to be inserted into a patient's body and positioned at a desired location adjacent an ROI. The manual control will perhaps include turning the tether to rotate the capsule and/or axially positioning the capsule and scanner relative to the ROI in the lumen, and possibly employing automated servo sensors, as indicated in a block 456 to facilitate the positioning of the capsule and one or more scanners at the desired location. Once positioned, automatic vibration compensation for the scanner can be provided, as noted in a block 452, to stabilize the image in regard to biological motion (breathing and cardiovascular movement) and physical movement of the patient. In addition, other mechanisms can be provided in at least one exemplary embodiment, for stabilizing the capsule where desired within the lumen of a patient's body.

Details of the various functions that can be implemented with the capsule imaging system are as follows:

Integrated Imaging, Screening, and Diagnosis

Optical tissue imaging using UV, visible, and IR wavelengths;
Fluorescence imaging using UV, visible, and IR wavelengths;
Thermal imaging using IR wavelengths;
Deep tissue imaging using IR wavelengths;
Concentric confocal and true confocal imaging;
Imaging through blood using IR wavelengths;
Polarization-contrast imaging;
Laser feedback microscopy;
Optical coherence tomography (OCT) and reflectometry (OCR);
Optically stimulated vibro-acoustography analysis;
High resolution and magnification tissue-contact imaging;
Laser-induced fluorescence (LIF) and ratio fluorescence imaging and detection;
Multi-photon excitation fluorescence imaging;
Fluorescence lifetime imaging and analysis;
True sizing of imaged structures using stereo and range finding options;
Laser-induced fluorescence spectroscopy (LIFS);
Raman spectroscopy analysis;
Elastic scattering spectroscopy (ESS) analysis;
Absorption spectroscopy;
Detection and mapping of chemi-luminescence and cell viability;
Spatial mapping of optical sensor data (oxygen concentrations, pH, ionic concentrations, etc.);
Temperature measurement and feedback control;
Guidance of pressure measurements (manometry) and correlation of visual and manometric observations of the esophagus, lower esophageal sphincter, stomach, pylorus, small intestine and other body lumens; and
Other measurements such as color, laser power delivery, tissue properties, photobleaching, and photocreation of compounds for monitoring and feedback control.

Therapies, Surgeries, and Monitoring

Photodynamic Therapy (PDT);
Heating of tissue and/or tumors, (e.g. hyperthermia treatment);
Laser surgery from optical illumination (UV, heat, and/or ablation)
Photoactivated chemistry, photopolymerization, and implantation of biomaterials;
Laser cauterization; and
Mechanical destruction of tissue using shock waves produced by absorption of pulsed optical radiation.

Interactive Displays & Advanced User Interface Design

Quasi-stereo on display monitors, stereographic mapping using pseudo color overlay, and true 3D display formats (Note: Individual display strategies and capabilities depend on the specific application); and
Interactive touch/point screen.

FIGS. 11A and 11B illustrate the different functions that can be carried out with the capsule, depending upon the instrumentation that is used in the scanning system. FIG. 11A shows a single scanning waveguide used for imaging, sampling diagnoses, and administering therapy, while in FIG. 11B, the single scanning waveguide is used for 3D imaging, obtaining a tissue biopsy, and monitoring endoscopic surgery. While in both these Figures, many of the components are identically provided, it is helpful to recognize that by making small modifications to the components that are used as part of the system, different functionality can be provided. In a system 460 shown in FIG. 11A, an interactive computer workstation monitor 462 enables medical practitioners to control the scanning optical fiber and to execute software algorithms used for imaging, diagnosis (e.g., optical biopsy), and administering therapy. A high resolution color monitor 464 receives signals from a scanning optical fiber 484 that are conveyed over an optical fiber system 488 to a distribution console 472. Optional RGB detectors may be provided if not included internally within the patient's body adjacent to scanning optical fiber 484. An ROI 486 is scanned by the optical fiber to produce the high resolution color images displayed to a user. In an exemplary passive display embodiment, two cathode ray tube monitors (CRTs) display images using two different contrast modes to generate the images of the same object (e.g., tissue). For example, the same resonant driven scanning optical fiber may produce both a full-color optical image on one CRT and a grayscale fluorescence image on the other CRT monitor. If the optical properties of the excitation and signal do not overlap, then two or more images may be generated simultaneously. Otherwise, the two images are either captured in a frame sequential method or in alternating line sweeps of the fast resonant scanner. To switch between image contrast modes (full-color optical and fluorescence), the light sources are shuttered or directly turned off/on. Synchronized in time during the modulation of both illumination power and spectral range, the signals from the photon detectors are recorded and displayed as separate images. In this example, having a second fluorescence image of the same ROI, a medical practitioner can find and positively identify small or precancerous lesions that may or may not be visible on a standard white-light image.

It is contemplated that one of the two displays might be interactive, such as by using a touch screen monitor or interactive foot mouse or pedal that enables the medical practitioner to select (draw the outline of) an ROI for laser surgery. Since the image may be moving, the touch screen monitor will require the image to be captured and frozen in time. However, once this ROI is outlined, image segmentation and object recognition algorithms may be implemented to keep the ROI highlighted during real-time image acquisition and display. The interactive monitor can provide sidebar menus for the practitioner to set parameters for the laser therapies, such as power level and duration of laser radiation exposure. The second display would not be used interactively, but is preferably a high resolution monitor displaying the real-time optical image in full-color or grayscale. If IR photon detectors are integrated into the endoscope, the high resolution display with pseudo-color will allow the practitioner to monitor the progress of laser therapies, such as tissue heating and/or tissue irradiation in laser surgery.

The scanning optical fiber within the capsule is positioned at a desired location within the patient's body, opposite ROI 486, using the tether and an optional manual controller that facilitates tip navigation and stabilization, as indicated in a block 466. The disposition of the capsule within the lumen can be automatically determined based upon a position sensor signal or simply by monitoring the distance that the tether extends into the lumen, with reference to a scale provided on the tether, as discussed below in connection with FIG. 13. Within ROI 486, optical biopsy "spots" 485 illustrate the spatial and temporal distribution of single-point spectral measurements to diagnose for disease. These spots are distributed much like the current practice of invasively taking tissue samples for in vitro biopsy analysis. Each spot may be analyzed spectroscopically during a frame cycle of the optical scanner, separating $t_1$ and $t_2$ by, for example, about 1/30 second. In addition to the image provided by the scanning optical fiber, IR thermal photodetectors (and an optional temperature monitor) as indicated in a block 468 could be included for receiving IR signals from the ROI.

To facilitate control of the motion of the scanning optical fiber or light waveguide, electrical power for microsensors and control electronics are provided, as indicated in a block 470. The signals provided by the control electronics enable amplitude and displacement control of the optical fiber when the actuator that causes it to scan is controlled by both electrical hardware and software within block 470. A spectrophotometer and/or spectrum analyzer 474 is included for diagnostic purposes, since the spectral composition of light received from ROI 486 and distribution of optical biopsy spots 485 can be used for screening and diagnosis for such diseases as cancer by a medical practitioner evaluating the condition of the ROI in the lumen, based upon spectral photometric analysis. To illuminate the ROI so that it can be imaged, red, green, and blue light sources 476, 478, and 480 are combined and the light that they produce is conveyed through the optical fiber system to scanning optical fiber 484 within the capsule. The light source used for spectral analysis may be a high power pulse from one of the external RGB light sources (e.g., lasers), or a secondary laser or white light source. Since signal strength, time, and illumination intensity are limiting, a repeated single-point spectroscopic method will be initially employed, using flash illumination. In addition, the same or a different high power laser source 482 can be employed to administer therapy, such as PDT, the laser ablation of dysplasia, neoplasia, and tumors, and other types of therapy rendered with a high intensity source.

In using system 460, a medical practitioner navigates and maneuvers the flexible tether and attached capsule that includes the scanner, to an appropriate region of the lumen in a patient's body while watching the high resolution color monitor displaying the standard, full-color endoscopic image. The search for tumors, neoplasia, and/or pre-cancerous lesions in the lumen can begin by simply watching the monitor. A second monitor (not separately shown) included with spectrophotometer and spectrum analyzer 474 displays a fluorescence mapping in pseudo-color over a grayscale version of the image produced by the scanner in the capsule. When abnormal appearing tissue is found, the capsule is optionally mechanically stabilized (e.g., by inflating an attached balloon, as explained below). The ROI on the lumen wall is centered within the FOV of the scanner, then magnified using a multi-resolution capability provided by the scanner. The size of the ROI or cancer is estimated and a pixel boundary is determined by image processing either the visible image or the fluorescence image. If spectroscopic diagnosis is required, such as LIFS, the distribution of optical biopsy points is estimated along with illumination levels. The diagnostic measurements are performed by automatically delivering the illumination repeatedly over many imaging frames. The user can cease the diagnosis or have the workstation continue to improve signal-to-noise ratio and/or density of sampling until a clear diagnosis can be made from the images produced of the lumen inner surface by the scanner in the capsule. The results of diagnosis is expected to be in real-time and overlaid on top of the standard image.

If optical therapy is warranted, such as PDT, then an optical radiation exposure is determined and programmed into the interactive computer workstation controlling the scanner system in the capsule. The PDT treatment is an optical scan of high intensity laser illumination typically by high power laser source 482, pre-selected for the PDT fluorescent dye, and is controlled using dichroic filters, attenuators, and electromechanical shutters, as explained above. In a frame-sequential manner, both fluorescence images and visible images are acquired during PDT treatment rendered using the scanner in the capsule. The medical practitioner monitors the progress of the PDT treatment by observing these images acquired with the scanner, on both displays.

With reference to FIG. 11B, a scanning system 460' provided in a capsule is used for 3D imaging, biopsy, and monitoring endoscopic surgery of an inner surface of a lumen. To enable 3D imaging in a pseudo-stereo view of the ROI, an HMD 490 is included. In addition, the system includes high resolution color monitor 464, which was described above in connection with FIG. 11A. Also, an IR optical phase detector 492 is included for range finding within the lumen. High frequency modulation of IR illumination can be measured to determine phase shifts due to optical propagation distances on the order of a few millimeters. The distance between the distal end of the scanning optical fiber or light waveguide in the capsule and ROI 486 can be important in evaluating the intensity of light that should be applied during endoscopic surgery, for mapping a specific ROI 487 to determine its boundary or size, and for determining the size and shape of features such as the area of dysplasia or volume of a tumor comprising the ROI in the lumen. An UV-visible biopsy light source 494 enables an optical biopsy to be carried out at specific ROI 487. The spectrophotometer and spectrum analyzer in block 474 are useful in monitoring the status of the ROI during the endoscopic surgery being carried out, since the condition of the ROI during the endoscopic surgery can sometimes best be determined based upon the spectrum analysis provided by this instrumentation. In other respects, the components used for the alternative functions provided in FIG. 11B are identical to those in FIG. 11A.

When using system 460', a medical practitioner again searches for neoplasia by moving the tether and capsule to reposition the scanner while watching high resolution color monitor 464, which shows the visible wavelength (full-color) image. When an ROI is found, the capsule can be mechanically stabilized, e.g., by inflating a balloon attached to it, as discussed below. Again, the ROI is centered within the FOV, and then magnified with the multi-resolution capability. However, if the surrounding tissue is moving so the acquired image is not stationary, a snapshot of the image is captured and transferred to the interactive computer workstation monitor, which is preferably an interactive display. The boundary of the stationary ROI is outlined on the interactive display screen, and an area of dysplasia or volume of the tumor is estimated from a diameter measurement in pixels and a distance measurement between the scanner and the tissue using IR optical phase detector 492 for range finding. An optical biopsy is taken with UV-visible biopsy light source 494, which can be an optical fiber-coupled arc lamp for elastic scattering spectroscopy (ESS). If warranted for this cancerous or pre-cancerous tissue, the optical radiation exposure is calculated, and a treatment protocol is programmed into interactive computer workstation monitor 462. Digital image processing algorithms can be calibrated for automatically segmenting the ROI or processing the scanner signal to eliminate motion artifacts from the acquired images in real-time, which may be equivalent or less than the display frame rate. The laser surgical treatment and/or cauterization can occur with high intensity laser 482 (IR) that is optically coupled with the visible optical scanner. If the IR range finding option is not required, but an IR temperature monitor or laser monitor is desired, then the IR source can instead be used for these alternative monitoring functions. In a frame-sequential manner, both the IR and visible images are acquired during the laser surgery and/or cauterization. The IR image is either a mapping of the back scatter from the laser illumination as it scans the ROI in the lumen, or a thermal image of the ROI, which can be displayed on the interactive computer display as pseudo-color over a grayscale visible image. The medical practitioner monitors the progress of the IR radiation treatment by observing these acquired images on both the high resolution and interactive display monitors.

Determining Disposition of Capsule in Body Lumen

An earlier exemplary embodiment of the scanning flexible endoscope employed a wheel that rotated with the axial movement of the tether as the tether was manipulated to control the position of the capsule within the esophagus of a patient. However, the use of a contact sensor of that type may be inaccurate if the presence of saliva, mucous or other bodily fluids causes the tether to slip on the rotating sensor wheel, so that the position of the capsule within the esophagus is not accurately reported. In addition, the requirement that friction be maintained between the tether and the rotating sensor wheel may interfere with the "feel" that medical personnel may want to experience when controlling the capsule with the tether. Accordingly, FIGS. 12 and 13 illustrate two alternative exemplary embodiments of non-contact sensors for measuring the relative disposition of the capsule within a body lumen such as the esophagus.

In FIG. 12, the proximal end of a tether 630 is illustrated, external to the mouth of a patient 636. It will be understood that although not shown in this Figure (or in FIG. 13), the distal end of tether 630 extends down into the esophagus of patient 636. Optical indicia 634 are axially disposed along at least a portion of tether 630 and depending upon the form of the indicia, can provide either an analog or a digital indication of the relative disposition of the tether, and thus, of the capsule, within the esophagus of patient 636. A representation of an exemplary analog optical pattern 680 is illustrated in FIG. 20A, while FIG. 20B illustrates a representation of an exemplary digital optical pattern 682.

Those of ordinary skill in the art will understand that many optical sensors are readily available to read either analog or digital encoded data provided on the indicia on the tether. For example, a light source (not separately shown) on an optical sensor 638 can be directed toward indicia 634. Alternatively, ambient light can be used to illuminate the indicia. Light reflected or scattered by the indicia on tether 630 is then received by optical sensor 638, which may include a photodiode or other appropriate photodetector—not separately shown in this Figure. Also, one or more lenses can be included in the optical sensor to focus the light source (if used) on the indicia and/or the received light on the photodetector. It is also contemplated that the light source may direct light through the indicia so that the transmitted light is received by a photodetector on the opposite side of the indicia from the light source. However, since that approach is less likely to be implemented because of issues related to transmission of light through the periphery of a tether, it is not shown in the drawings.

The optical sensor can employ ultraviolet, visible, or infrared light from a light emitting diode (or other appropriate light source) and can use an optical fiber (not shown) to convey the light from such a source toward the indicia on the tether. Similarly, another optical fiber (not shown) can be used to collect the light from the indicia and convey it toward the photodetector. Use of shorter wavelength light and higher numerical aperture lenses for the collection optical fiber can improve the spatial resolution with which the indicia are read on the tether. The indicia can be applied axially around the entire circumference of at least a portion of the tether, so that the indicia can be read by the optical detector regardless of the rotational orientation of the tether about its longitudinal axis.

In FIG. 13, the indicia on tether 630 comprise a magnetic media 642, for example, a magnetic paint or tape, that is applied along the longitudinal axis of the tether for at least a portion of its length. The magnetic media can store a varying magnetic field that represents either analog or digital data indicating a relative position of the tether and thus, the capsule within a body lumen such as the esophagus, when the data are detected or read by a magnetic sensor 640. Magnetic sensor 640 can include a sensitive magnetic pickup coil (not separately shown) like those used in tape recorder heads. The magnetic media can encode the position data as analog or digital data, using varying magnetic intensity, modulation, frequency, or a combination of these types of encodings. It is also contemplated that the magnetic encoding can be read by the magnetic sensor, and its signal can be used to indicate both a relative position of the capsule in a visual display as well as providing an audible pitch that changes to indicate the relative position of the capsule in the body lumen.

The relative position of the tether and the capsule in a body lumen can be important for several reasons. First, the medical practitioner can relate the condition of the internal surface of body lumen that is evident in the images being produced by the image scanner included in the capsule with the position of the capsule in the body lumen, so that a condition such as BE as a specific location in the body lumen is clearly known. With this information, the same location in the body lumen can subsequently be accessed for further diagnostic procedures or to render a therapy. FIG. 14 illustrates how a non-contact position sensor 646 (such as the optical or magnetic sensors of FIGS. 12 and 13) reads the indicia on tether 652 to produce a position signal that is input to a processor in SFE base station 394. A position determination function 648 is implemented by the processor to determine at least a relative position of a capsule 650 within the body lumen at any given time. At the same time, the capsule is producing an image signal with its image scanning device that is input to an image creation function 662 carried out by the processor in the SFE base station. Not only does the relative position of the capsule enable indexing with the position of a current image produced by the scanning device in the capsule, it can also be used for assisting the processor in the SFE base station to more efficiently stitch together successive axial images to implement a stitched mosaic image creation function 664. While these successive axial images can be stitched together without the relative position data provided by non-contact position sensor 646, it can reduce the processing time required to determine where the longitudinal axial edges of successive images should be joined in the stitching process to create the axially continuous mosaic image that shows the internal surface of a body lumen along a substantial portion of its length.

The data provided by position determination function 648 can indicate the actual distance that the capsule has moved from a reference position to any subsequent position. For example, if a reference position for the capsule corresponding to its disposition at the gastroesophageal junction is determined from images produced by the capsule, subsequent motion of the capsule up the esophagus can be expressed as an actual distance from that reference position using the signal produced by non-contact position sensor 646. Thus, once this reference position is determined, the distance from the reference position to a region on the internal surface of the esophagus where apparent BE conditions are observed in the images can be determined from the position data. This region can then be readily found again by repeating the step of establishing the reference and advancing the capsule upwardly the same distance noted previously.

Optionally, it may be desirable to gently clean bodily fluids such as saliva and mucous from tether 652 as it is pulled from the body lumen or esophagus, before the bodily fluids on the tether reach non-contact position sensor 646. As illustrated in FIG. 15, an elastomeric cone 670 or other type of scraper fitted over tether 652 can wipe bodily fluids 672 from the tether outer surface without applying any significant friction to the tether that would interfere with the medical practitioner feeling its motion through the body lumen. The bodily fluids can simply drip onto an absorbent material or sponge (not shown) or can be collected in a small tray (also not shown) as drips 674 fall away from the peripheral lower edge of the elastomeric cone.

Use of a Balloon Coupled to Capsule

FIG. 16 illustrates a capsule 570 that has an inflatable balloon 574 coupled to its proximal end. The balloon does not interfere with illuminating light 572 being directed from the distal end of the capsule to an inner surface 582 of the lumen in which the capsule is disposed. A volume 586 within balloon 574 is selectively inflated with fluid or air that is conveyed through a lumen 578 within a tether 576. The fluid exits lumen 578 through at least one opening 588 that is formed in the portion of the tether encompassed by the balloon.

The balloon can be inflated to serve one or more distinct purposes, as follows. For example, balloon 574 can be inflated so that peristaltic muscle tissue action advances the balloon and the capsule through the lumen; the larger diameter of the balloon enables the force applied by the muscle tissue to more efficiently advance the balloon and the connected capsule through the lumen. As a further option, the balloon, when inflated, can convey a pressure from a wall of a lumen in which the balloon is disposed, to a pressure sensor (not shown here—but discussed above) that is on the capsule or otherwise in fluid communication with interior volume 586, so that the pressure exerted by the lumen wall can be monitored externally of the lumen. The pressure can be determinative of various conditions or provide other information of interest to a clinician.

Instead of enabling the capsule to advance, the balloon can be at least partially inflated to enlarge a cross-sectional size of the balloon, thereby preventing further movement of the capsule through a portion of a lumen or other passage having a cross-sectional size that is smaller than that of the balloon. Finally, the balloon can be inflated to generally center and stabilize the capsule within a lumen of the patient's body so that scanning of the inner surface of the lumen to produce images can be more effectively carried out.

Electrical Contacts to Stimulate Peristalsis

A capsule 590 is shown within a lumen 592 in FIG. 17 and includes a plurality of electrical contacts 594 disposed on the outer surface of the housing of the capsule. Electrical contacts 594 are connected to leads 598, which extend within a passage 602 formed in a tether 600. The leads are coupled to an electrical power source (not shown). An electrical voltage is thereby selectively applied to electrical contacts 594 through leads 598, thereby contacting muscle tissue 604 and stimulating peristalsis in the muscle tissue of lumen 592, which advances the capsule through the lumen. Optionally, electrical contacts 596 that are connected to tether 600 proximal of capsule 590 can be employed in lieu of or in addition to electrical contacts 594 to stimulate peristalsis of the muscle tissue.

Mechanical Biopsy

FIG. 18 illustrates a capsule 620 that is coupled to a tether 624. Tether 624 includes an annular passage 622 within which one or more cytological brushes 626 or biopsy forceps (not shown) are controllably advanced to contact the inner surface of the lumen in which capsule 620 is disposed. Cytological brush 626 is advanced from annular passage 622 into contact with the tissue on the inner surface, so that cells of the tissue lining the lumen are transferred onto the bristles of the brush. The cytological brush is then withdrawn into the annular passage and after the capsule and tether are withdrawn from the lumen in the patient's body, the cell sample can be removed from the bristles for further processing and study. Although not shown, the annular passage can be used to pull back a flap on the capsule that exposes bristles that can be advanced from the capsule. Instead of an annular passage, the cytological brush, a fine needle, or other type of mechanical biopsy device can be advanced through a piggyback passage provided on the tether (not shown). A grasping device may also be employed in the annular or piggyback passage to gather a sample from the lumen and retract with the sample back into the passage. Such a passage can also be used as an intake for a fluid that is drawn through the passage to the proximal end of the tether that is outside the patient's body.

Multiple Images

As noted above, it is contemplated that a plurality of scanners can be included in the capsule, in accord with the present invention. Since each of the scanners are relatively small in size, they can be configured in a spaced-apart array that can image a large field of view, encompassing, for example, an entire 360° view of the inner surface of a lumen. Alternatively, as shown in FIG. 19, a single scanner can be used in a capsule 650, to image the four sides of a lumen 672 (including, the two sides shown, as well as the side behind the pyramidal mirror and the side opposite, neither of which is visible in this Figure). Capsule 650 is connected to a tether 652 that extends externally of lumen 672. A moving optical fiber 654 in the capsule emits light that is directed through a lens 656, toward a pyramidal-shaped mirror 658. The adjacent mirror surfaces of pyramidal mirror 658 reflect the light from lens 656 in the four different directions and through lenses 660a and 660b (the other two lenses not being shown). Light reflected from the inner surface of lumen 672 is detected by annular detectors 670a and 670b (the other two annular detectors not being shown). If the extent of overlap of the images provided on the four sides of capsule 650 is incomplete, a user can rotate tether 652, as indicated by an arrow 674, which will rotate capsule 650 to change the direction in which the scanning of the inner surface occurs, so that additional images can be produced and optionally connected together to form a full panoramic view of the inner surface of the lumen.

Multiple Tether/Capsule Position Sensors

To increase the precision and accuracy with which the relative position of the tether/capsule is measured, two optical or magnetic sensors can be used concurrently to read the indicia on the tether. Interpolation between the optical or magnetic scaling provided by the indicia can also be employed. The spacing of these two or more sensors will be precisely determined, and one sensor can be employed for measuring a full-step, while the other sensor is measuring a half-step. FIG. 21 illustrates an exemplary embodiment of a dual color encoding pattern 800 with dual sensors. To detect red analog or digital markings 818 on a tether 820, a red laser 802 produces red wavelength light that is directed either in free space, or as shown in this exemplary embodiment, through an optical fiber 822 toward a lens 806, which focuses the red light onto dual color encoding pattern 818. Red light reflected from the red portion of the dual color encoding pattern passes through a lens 808 and is conveyed either through free space, or as shown, through an optical fiber 824, to a red wavelength light photodetector 804. Similarly, on an opposite side of tether 820, a green laser produces light having a green wavelength that is conveyed in free space or through an optical fiber 826 toward a lens 814, which focuses the light onto dual color encoding pattern 818. Green light reflected from the green portion of the dual color encoding pattern passes through a lens 816 and through free space or as shown, through an optical fiber 828, which conveys the green light to a green light photodetector 812. Appropriate red and green bandpass filters (not shown) will likely be included in the respective red and green light photodetectors to limit the wavelength of the light reaching the photodetector photodiode. The red and green light photodetectors each produce position signals that are processed to effectively double the resolution with which the relative position of tether 820 and the capsule to which it is coupled is determined by the processor in the SFE base station. It would be desirable to be able to determine the relative position of the capsule in a body lumen such as the esophagus with a resolution of at least 1.0 mm. Instead of red and green light encoding and detection, other combinations of colored light can be used. For example, red and infrared light sources and photodetectors may be used, since the wavelengths of red and infrared light are within the peak sensitivity waveband (700-900 nm) of silicon photodiodes (which can be employed as the two different color photodetectors).

As another option, actual high-resolution scaling can be printed in optical contrast lettering on the tether, and the non-contact sensor can include an optical character reader that enables the processor in the SFE base unit to "read" the scaling at high spatial resolution. Further, the clinician can also visually directly read the scales on the tether, as well, during use of the tether for positioning the capsule in the body lumen.

FIGS. 22A and 22B illustrate details of a tether 830, which includes a supporting structure 832 around a central region 838 within which are disposed optical fibers, conductive wires, lumens, etc. On the outer surface of supporting structure 832 is a data layer 834 (i.e., the applied tape or markings that convey analog or digital position information). Finally a protective coating that is biocompatible and prevents abrasion or damage to the data layer overlies the data layer. The protective coating can comprise a clear polymer or other suitable clear, biocompatible material.

For use in screening for BE in the esophagus, a clinician will generally want to initially employ the scanning capability of the capsule for imaging the region immediately above and adjacent to the gastroesophageal junction where the esophagus is joined to the stomach. The average distance from the mouth of a patient down the esophagus to a position of the capsule suitable for scanning to produce images of this region is about 39 cm. To facilitate the initial positioning of the capsule, as shown in FIG. 23, tether 652 can be provided with a visible indication, such as a red mark 840 that is located about 39 cm above capsule 650. Thus, when the clinician observes that red mark 840 is disposed at about the lips of the patient, it will be evident that for the average patient, capsule 650 has been carried down the esophagus to the point immediately above the gastroesophageal junction. The clinician can confirm this position of the capsule by viewing the images of the region adjacent to the capsule at that point. Small adjustments can be made to the position of the capsule, as necessary, and additional differently colored visible marks 842 and 844 are provided on each side of red mark 840 to assist the clinician in keeping track of the small adjustments. Of course, the position signal produced by monitoring the data provided on the tether with the non-contact position sensor can also be employed for making small adjustments. Once the initial position related to the gastroesophageal junction has been determined, that position can then serve as a reference position in regard to the relative position determined from the position data on the tether.

FIGS. 24-26 illustrate three different exemplary embodiments that illustrate slightly different approaches for supplying a pulse of a fluid (typically, a pulse of air) to a position adjacent to the distal end of the tether or of the capsule. The pulse of fluid such as air can be employed to assist in more readily moving the capsule within the esophagus (or other body lumen) and in particular, in moving the capsule through the LES between the esophagus and the stomach. To facilitate free movement of the capsule within the esophagus and through the LES, an air pulse is supplied down a lumen within a tether 850 from a source of pressurized air (and a valve to provide the air pulse) via a tube 856. The lumen continues through the capsule and opens to the body lumen at an orifice

854 that is formed in the housing of a capsule 858. This bolus or air pulse is thus selectively delivered to the interior of the esophagus (or other body lumen) at a point adjacent to the capsule, causing the wall of the esophagus to be distended and the LES at the top of the stomach to autonomously open.

Another exemplary embodiment for delivering the air pulse shown in FIG. 25 includes a piggy-back tube that is attached along an external surface of tether 860 and has a distal port 864 disposed adjacent to the distal end of the tether, so that the air pulse is released into the esophagus adjacent to a capsule 866. Both exemplary embodiments shown in FIGS. 24 and 25 provide directional pulses of air, which can be used to force non-axially symmetric actions and reactions to the pneumatic pressure. The resultant motion of the capsule and reaction of the tissue can be controlled for maneuvering and positioning the capsule with respect to the lumen wall. In contrast, FIG. 26 illustrates an exemplary embodiment that uses a tether 870 as a guide wire for a larger tube 872 that exerts axially symmetric pressure from the fluid pulse. Tube 872 has an annular opening 876 disposed at its proximal end for receiving a pulse of pressurized air from a source and valve (neither shown) and another annular opening 874 at its distal end, which is adjacent to the distal end of the tether and to capsule 866, so that the pulse of air causes the LES to open and/or the internal wall of the esophagus or other body lumen in which the capsule is disposed to autonomously distend outwardly. Other techniques for delivering a pulse of air or other type of fluid can also be used for this purpose.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for monitoring a relative position of a scanning capsule within a body lumen of a patient, where the scanning capsule is coupled to a flexible tether that extends externally of the body lumen, comprising the steps of:
   (a) providing the scanning capsule comprising a scanning device disposed within a capsule housing, wherein the scanning capsule is coupled to the flexible tether having indicia along an axial length of at least a portion of the flexible tether, wherein the indicia are indicative of a position along the axial length of the flexible tether, and wherein the flexible tether is (1) smaller in diameter than the scanning capsule, (2) of sufficient strength to retract the scanning capsule from the body lumen, and (3) of sufficient flexibility to permit advancement of the scanning capsule along the body lumen with normal peristalsis;
   (b) introducing the scanning capsule and at least a portion of the flexible tether into the body lumen of the patient by swallowing, wherein the scanning capsule advances along the body lumen with the normal peristalsis;
   (c) driving the scanning device in a scanning pattern so as to scan a beam of light onto at least a portion of the body lumen;
   (d) detecting light reflected from the at least the portion of the body lumen using a light sensor; and
   (e) determining the relative position of the scanning capsule within the body lumen with the indicia on the flexible tether by sensing the indicia with a first optical sensor and a second optical sensor, wherein the indicia comprise markings of at least two different colors, and wherein the first optical sensor is responsive to light from the indicia of one color and the second optical sensor is responsive to light from the indicia of another color.

2. The method of claim 1, further comprising the step of providing at least one non-numeric visible reference mark on the flexible tether to indicate an expected reference position, to enable a user to manually position the scanning capsule at about a desired location based upon a visual indication provided by the at least one non-numeric visible reference mark on the flexible tether.

3. The method of claim 2, wherein the body lumen comprises an esophagus, and wherein the expected reference position corresponds to a position on the flexible tether that should indicate when the scanning capsule is expected to be disposed at about a gastroesophageal junction in the esophagus.

4. The method of claim 1, wherein the first and second optical sensors are configured to produce a position signal indicative of a position of the flexible tether in response to an optical parameter that varies along the axial length of the flexible tether.

5. The method of claim 4, wherein the position signal comprises either a digital position signal or an analog position signal indicative of a current position along the axial length of the flexible tether adjacent to one or more of the first optical sensor or the second optical sensor, the indicia provided along the axial length of the flexible tether comprising an optical code so that the position signal is produced in response to at least one parameter selected from the group consisting of:
   (a) a color of the optical code that is sensed by one or more of the first or second optical sensors;
   (b) a digital value indicated by the optical code;
   (c) an intensity of light reflected from the optical code compared to an intensity of light reflected from a background area;
   (d) a pattern of the optical code that conveys digital information;
   (e) a relative size of markings comprising the optical code;
   (f) a shape of the markings comprising the optical code;
   (g) a scattering of light by the optical code compared to a scattering of light from the background area; and
   (h) a wavelength of light reflected by or absorbed by the optical code.

6. The method of claim 1, further comprising the step of providing the first and second optical sensors to monitor the indicia on the tether to increase a resolution with which the relative position of the scanning capsule in the body lumen is determined.

7. The method of claim 1, further comprising the step of applying the indicia by a step selected from the group of steps consisting of: affixing the indicia to the flexible tether as a longitudinally extending tape, and applying the indicia to the flexible tether as a longitudinally extending coating.

8. The method of claim 1, further comprising the step of protecting the indicia with a protective coating applied over the indicia.

9. The method of claim 1, further comprising the step of providing a scraper for wiping bodily fluids from the flexible tether as the flexible tether is withdrawn from the body lumen.

10. The method of claim 1, further comprising the step of determining a reference position for the scanning capsule within the body lumen relative to which the indicia are used to determine the relative position of the scanning capsule as the scanning capsule and the flexible tether are moved within the body lumen.

11. The method of claim 10, wherein the step of determining the reference position comprises the step of moving the scanning capsule to a known position within the body lumen as determined by inspecting images of an interior surface of the body lumen, a disposition of the scanning capsule at said known position comprising the reference position used to determine subsequent positions of the scanning capsule as the flexible tether is used to move the scanning capsule within the body lumen.

12. The method of claim 1, wherein the scanning device comprises a optical fiber that is driven in the scanning pattern.

13. The method of claim 1, wherein the scanning capsule is about 7 mm in diameter and the flexible tether is about 1 mm in diameter.

14. An apparatus for measuring a relative position in a body lumen of a capsule used for scanning an inner surface of the body lumen to produce images of the inner surface, comprising:
(a) a capsule comprising a scanning device disposed within a capsule housing, wherein the capsule is sized to be introduced into the body lumen by swallowing and advanced along the body lumen with normal peristalsis;
(b) a flexible tether having a distal end coupled to the capsule and a proximal end that is adapted to connect to a system for receiving an imaging signal produced by the capsule that is conveyed through the flexible tether, the flexible tether being (1) smaller in diameter than the capsule, (2) of sufficient strength to retract the capsule from the body lumen, and (3) of sufficient flexibility to permit advancement of the capsule along the body lumen with the normal peristalsis, the flexible tether including indicia disposed axially along the flexible tether for indicating a position of the flexible tether as the flexible tether is moved through the body lumen, and thus indicating a position of the capsule within the body lumen, wherein the indicia comprise markings of at least two different colors;
(c) an actuator driving the scanning device in a scanning pattern so as to scan a beam of light onto at least a portion of the body lumen; and
(d) a light sensor detecting light reflected from the at least the portion of the body lumen;
(e) a first optical sensor configured to respond to light from the indicia of one color; and
(f) a second optical sensor configured to respond to light from the indicia of another color.

15. The apparatus of claim 14, wherein the first and second optical sensors are configured to respond to a light signal received from the indicia included on the flexible tether that is indicative of the position of the flexible tether and of the capsule within a body lumen, the light signal encoding an axial position of the flexible tether in at least one form selected from the group consisting of:
(a) a color of the light signal that is sensed by one or more of the first or second optical sensors;
(b) a digital value indicated by the light signal received from the indicia;
(c) an intensity of the light signal comprising light reflected from the indicia, compared to an intensity of light reflected from a background area;
(d) an optically perceptible pattern of the indicia that conveys digital information;
(e) a relative size of markings comprising the indicia;
(f) a shape of the markings comprising the indicia;
(g) a scattering of light by the indicia compared to a scattering of light from the background area; and
(h) a wavelength of light reflected by or absorbed by the indicia.

16. The apparatus of claim 15, wherein one or more of the first or second optical sensors include a lens for focusing the light signal received from the indicia.

17. The apparatus of claim 15, wherein one or more of the first or second optical sensors include a lens for focusing light directed toward the indicia from a light source.

18. The apparatus of claim 15, wherein one or more of the first or second optical sensors include an optical fiber for conveying light at least one of to or from the indicia.

19. The apparatus of claim 15, wherein the indicia comprise an encoded pattern that repeats at least once along an axial length of the flexible tether.

20. The apparatus of claim 15, wherein the first optical sensor is disposed at an opposite side of the flexible tether from the second optical sensor, so that both optical sensors respond to the indicia to increase a resolution with which the position of the flexible tether and the capsule within the body lumen is determined.

21. The apparatus of claim 20, wherein the first and second optical sensors each sense a different characteristic of the indicia.

22. The apparatus of claim 14, further comprising a scraper that is disposed along the tether, and is configured to wipe bodily fluids from the flexible tether as the flexible tether is withdrawn from the body lumen.

23. The apparatus of claim 14, wherein the first and second optical sensors are configured to produce a position signal indicating a position of the flexible tether and the capsule within the body lumen, and wherein the apparatus further comprises a processor that is coupled to the first and second optical sensors for processing the position signal produced by the first and second optical sensors to indicate a distance between the capsule and a reference position within the body lumen.

24. The apparatus of claim 14, further comprising a protective coating applied over the indicia, the protective coating comprising a material that is biocompatible and protects the indicia from mechanical damage and abrasion.

25. The apparatus of claim 14, wherein the scanning device comprises a optical fiber that is driven in the scanning pattern.

26. The apparatus of claim 14, wherein the capsule is about 7 mm in diameter and the flexible tether is about 1 mm in diameter.

27. An apparatus for measuring a relative position in a body lumen of a capsule used for scanning an inner surface of the body lumen to produce images of the inner surface, comprising:
(a) a tether having a distal end coupled to the capsule and a proximal end that is adapted to connect to a system for receiving an imaging signal produced by the capsule that is conveyed through the tether, the tether being smaller in diameter than the capsule, the tether including indicia disposed axially along the tether for indicating a position of the tether as the tether is moved through the body lumen, and thus indicating a position of the capsule within the body lumen;
(b) a first optical sensor that automatically senses and responds to the indicia disposed on the tether without requiring contact with the tether, to produce a position signal indicating a position of the tether and the capsule within the body lumen; and
(c) a second optical sensor, wherein the indicia comprise markings of at least two different colors, and wherein the first optical sensor is responsive to light from the indicia of one color, while the second optical sensor is responsive to light from the indicia of another color.

28. An apparatus for measuring a relative position in a body lumen of a capsule used for scanning an inner surface of the body lumen to produce images of the inner surface, comprising:

(a) a tether having a distal end coupled to the capsule and a proximal end that is adapted to connect to a system for receiving an imaging signal produced by the capsule that is conveyed through the tether, the tether being smaller in diameter than the capsule, the tether including indicia disposed axially along the tether for indicating a position of the tether as the tether is moved through the body lumen, and thus indicating a position of the capsule within the body lumen;

(b) a first optical sensor that automatically senses and responds to the indicia disposed on the tether without requiring contact with the tether, to produce a position signal indicating a position of the tether and the capsule within the body lumen; and (c) a second optical sensor that is disposed at an opposite side of the tether from the first optical sensor, so that the first and second optical sensors both respond to the indicia, to increase a resolution with which the position of the tether and the capsule within a body lumen is determined, wherein the first and second optical sensors each sense a different characteristic of the indicia.

\* \* \* \* \*